(12) United States Patent
Burton et al.

(10) Patent No.: US 12,417,904 B2
(45) Date of Patent: Sep. 16, 2025

(54) EFFECTIVE USE OF MULTIPLE CHARGE STATES

(71) Applicant: DH TECHNOLOGIES DEVELOPMENT PTE. LTD., Singapore (SG)

(72) Inventors: Lyle Lorrence Burton, Woodbridge (CA); Eva Duchoslav, Toronto (CA)

(73) Assignee: DH TECHNOLOGIES DEVELOPMENT PTE. LTD., Singapore (SG)

( * ) Notice: Subject to any disclaimer, the term of this patent is extended or adjusted under 35 U.S.C. 154(b) by 395 days.

(21) Appl. No.: 18/007,499

(22) PCT Filed: Aug. 12, 2021

(86) PCT No.: PCT/IB2021/057443
§ 371 (c)(1),
(2) Date: Jan. 31, 2023

(87) PCT Pub. No.: WO2022/034535
PCT Pub. Date: Feb. 17, 2022

(65) Prior Publication Data
US 2023/0282468 A1 Sep. 7, 2023

Related U.S. Application Data

(60) Provisional application No. 63/064,560, filed on Aug. 12, 2020.

(51) Int. Cl.
*H01J 49/00* (2006.01)
*H01J 49/42* (2006.01)

(52) U.S. Cl.
CPC ...... *H01J 49/0036* (2013.01); *H01J 49/4295* (2013.01); *H01J 49/4215* (2013.01)

(58) Field of Classification Search
CPC ............... H01J 49/0027; H01J 49/0031; H01J 49/0036; H01J 49/4295; H01J 49/4215
See application file for complete search history.

(56) References Cited

U.S. PATENT DOCUMENTS 5,072,115 A 12/1991 Zhou
5,352,891 A 10/1994 Monnig et al.
(Continued)

FOREIGN PATENT DOCUMENTS

| EP | 3193174 A1 | 7/2017 |
|---|---|---|
| GB | 2464795 A | 5/2010 |
| WO | 2020157720 A1 | 8/2020 |

OTHER PUBLICATIONS

International Search Report and Written Opinion for PCT/IB2021/057443, mailed Nov. 15, 2021.

*Primary Examiner* — David E Smith
(74) *Attorney, Agent, or Firm* — Potomac Law Group, PLLC; Reza Mollaaghababa; Ido Rabinovitch

(57) ABSTRACT

At least one molecule is ionized and a mass spectrometer mass analyzes an m/z range, producing an m/z mass spectrum. A range of N sequential charge states is received. A copy of the m/z mass spectrum is created for each of the N charge states, producing N m/z spectra. Each spectrum of the N spectra is converted to a neutral mass mass spectrum using a different charge state of the N charge states, producing N neutral mass mass spectra. The N neutral mass mass spectra are aligned by neutral mass. When two or more spectra of the N neutral mass mass spectra corresponding to two or more different and sequential charge states include a neutral mass peak above a predetermined intensity threshold at a neutral mass value within a predetermined neutral mass tolerance, the neutral mass value is identified as a neutral mass of the at least one molecule.

15 Claims, 26 Drawing Sheets

(56) References Cited

U.S. PATENT DOCUMENTS

2018/0301326 A1* 10/2018 Bern ................. G06N 3/126
2019/0103259 A1* 4/2019 McIntosh ............ H01J 49/165

* cited by examiner

EFFECTIVE USE OF MULTIPLE CHARGE STATES

RELATED US APPLICATIONS

This application claims priority from U.S. Provisional Patent Application Ser. No. 63/064,560, filed on Aug. 12, 2020, the entire contents of which is hereby incorporated by reference herein.

INTRODUCTION

The teachings herein relate to identifying molecular weight (MW) or neutral mass values of at least one molecule in mass spectrometry (MS). More particularly, the teachings herein relate to systems and methods for identifying MW or neutral mass values of at least one molecule in MS by converting a mass-to-charge ratio (m/z) mass spectrum to an MW or neutral mass mass spectrum using a range of sequential charge states. The systems and methods disclosed herein can be performed in conjunction with a processor, controller, microcontroller, or computer system, such as the computer system of FIG. 1.

Analysis of Large Molecules by ESI-MS

Both quantitative and (especially) qualitative analysis of larger molecules by ESI-MS present a number of challenges. One challenge is the fact that a single chemical form is spread over many sequential charge states. The presence of isotopes and adducts further complicates the situation. The different charge states for these forms can partially or more significantly overlap in the m/z dimension.

Spectral peak-finding algorithms process each peak or at least each isotope cluster as an independent entity and do not make use of the fact that there is additional information available in the related charge states. In other words, current spectral peak-finding algorithms that find an isotopic pattern in one charge state do not look for the pattern in another charge state. As a result, identifying or confirming a peak in a mass spectrum of a large molecule is a difficult and time-consuming process.

For example, conventionally it is very difficult to see separate isotopes in the spectra of very large molecules. The isotopes are there, but they are difficult or impossible to resolve with given MS technology. Similarly, when current mass spectrometer software converts peaks from the m/z dimension to the MW dimension it is often difficult to determine which MW peaks are real. This is because these maximum entropy or Bayesian algorithms often generate artifacts which are not real.

As a result, confirming a peak currently involves following an arduous manual process. First, a mass is selected. For example, a particular MW is selected. Then the mass spectrum is interrogated to determine if there are m/z peaks for the selected MW at many different and sequential charge states. Typically, this is very difficult to determine without constantly zooming in and out of the mass spectrum. Consequently, it is a time-consuming process.

Note that Molecular Weight or MW usually refers to the average mass of a compound (the weighted average of all of its isotopes). As a result, when constructing plots, the x-axis generally refers to "Neutral Mass" and not MW. For the case of a larger molecule where the isotopes are not resolved, the mass can be referred to as MW. However, for a molecule with resolved isotopes, neutral mass is a more precise term for each isotope mass. The mass of the first (monoisotopic) isotope is referred to as M0, for example. Consequently, the terms "neutral mass" and "MW" are used interchangeably throughout this written description.

FIG. 2 is an exemplary plot 200 of a mass spectrum of a large molecule (an antibody) showing the location in the m/z dimension of a selected MW mass at different charge states as displayed by conventional mass spectrometer software. In FIG. 2, the selected MW mass is 148,274 Da. Points 210 show the location in the m/z dimension of mass 148,274 Da at sequential charge states +40 to +65.

FIG. 3 is an exemplary plot 300 of a reconstructed and deconvoluted MW mass spectrum corresponding to the mass spectrum of FIG. 2 as displayed by conventional mass spectrometer software. In FIG. 3, it is unclear if peak 310 near the selected MW mass of 148,274 Da is actually present in the data or is an artifact of the algorithm. It is not possible to manually confirm the correctness of this MW without considerable zooming of the spectrum shown in FIG. 2 to view individual charge states in more detail.

FIG. 4 is an exemplary plot 400 showing the zoomed section of the mass spectrum of FIG. 2 that includes charge states +59 and +58 as displayed by conventional mass spectrometer software. There appears to be no evidence of a peak in the +59 cluster near the expected m/z of MW mass 148,274 Da represented by point 410. Similarly, there appears to be no evidence of a peak in the +58 cluster near the expected m/z of MW mass 148,274 Da represented by point 420.

FIG. 5 is an exemplary plot 500 showing the zoomed section of the mass spectrum of FIG. 2 that includes charge state +44 as displayed by conventional mass spectrometer software. FIG. 5 does appear to show some weak evidence of a peak in the +44 cluster near the expected m/z of MW mass 148,274 Da represented by point 510. Based on the weak evidence for charge state +44, a user would further interrogate sequential charge states +43 and +45 for additional evidence. Additional evidence of the expected m/z of MW mass 148,274 Da in sequential charge states is needed to confirm the presence of MW mass 148,274 Da.

FIGS. 2-5 show how difficult it can be to confirm the presence of an MW mass peak of a large molecule using conventional mass spectrometry methods and systems. As a result, additional systems and methods are needed to confirm the presence of an MW mass peak of a large molecule when such a peak is spread over many sequential charge states by ESI-MS.

Background on Mass Spectrometry Techniques

Mass spectrometers are often coupled with chromatography or other separation systems, such as ion mobility, in order to identify and characterize eluting known compounds of interest from a sample. In such a coupled system, the eluting solvent is ionized and a series of mass spectra are obtained from the eluting solvent at specified time intervals called retention times. These retention times range from, for example, 1 second to 100 minutes or greater. The series of mass spectra form a chromatogram, or extracted ion chromatogram (XIC).

Peaks found in the XIC are used to identify or characterize a known peptide or compound in the sample. More particularly, the retention times of peaks and/or the area of peaks are used to identify or characterize (quantify) a known peptide or compound in the sample.

In traditional separation coupled mass spectrometry systems, a precursor ion or a product ion (fragment ion) of a known compound is selected for analysis and is mass analyzed at each time interval of the separation. In mass spectrometry (MS), an MS scan is performed at each interval of the separation for a mass range that includes the precursor ion. An MS scan includes the selection of a precursor ion or precursor ion range and mass analysis of the precursor ion or precursor ion range.

In tandem mass spectrometry or mass spectrometry/mass spectrometry (MS/MS), an MS/MS scan is performed at each interval of the separation for a mass range that includes the product ion. An MS/MS scan includes the selection of a precursor ion or precursor ion range, fragmentation of the precursor ion or precursor ion range, and mass analysis of the resulting product ions. For both separation coupled MS and separation coupled MS/MS, the intensity of the ions found in each is collected over time and analyzed as a collection of spectra, or an XIC, for example.

Both MS and MS/MS can provide qualitative and quantitative information. In MS, the precursor ion spectrum can be used to identify a molecule of interest. In MS/MS, the product ion spectrum can be used to identify a molecule of interest. In MS and MS/MS, the intensity of one or more ions can be used to quantitate the amount of the compound present in a sample.

A large number of different types of experimental methods or workflows can be performed using a tandem mass spectrometer. Three broad categories of these workflows are targeted acquisition, information-dependent acquisition (IDA) or data-dependent acquisition (DDA), and data-independent acquisition (DIA).

In a targeted acquisition method, one or more transitions of a precursor ion to a product ion are predefined for a compound of interest. As a sample is being introduced into the tandem mass spectrometer, the one or more transitions are interrogated or monitored during each time period or cycle of a plurality of time periods or cycles. In other words, the mass spectrometer selects and fragments the precursor ion of each transition and performs a targeted mass analysis only for the product ion of the transition. As a result, an intensity (a product ion intensity) is produced for each transition. Targeted acquisition methods include, but are not limited to, multiple reaction monitoring (MRM) and selected reaction monitoring (SRM).

In an IDA method, a user can specify criteria for performing an untargeted mass analysis of product ions, while a sample is being introduced into the tandem mass spectrometer. For example, in an IDA method, a precursor ion or mass spectrometry (MS) survey scan is performed to generate a precursor ion peak list. The user can select criteria to filter the peak list for a subset of the precursor ions on the peak list. MS/MS is then performed on each precursor ion of the subset of precursor ions. A product ion spectrum is produced for each precursor ion. MS/MS is repeatedly performed on the precursor ions of the subset of precursor ions as the sample is being introduced into the tandem mass spectrometer.

In proteomics and many other sample types, however, the complexity and dynamic range of compounds are very large. This poses challenges for traditional targeted and IDA methods, requiring very high-speed MS/MS acquisition to deeply interrogate the sample in order to both identify and quantify a broad range of analytes.

As a result, DIA methods, the third broad category of tandem mass spectrometry, were developed. These DIA methods have been used to increase the reproducibility and comprehensiveness of data collection from complex samples. DIA methods can also be called non-specific fragmentation methods. In a traditional DIA method, the actions of the tandem mass spectrometer are not varied among MS/MS scans based on data acquired in a previous precursor or product ion scan. Instead, a precursor ion mass range is selected. A precursor ion mass selection window is then stepped across the precursor ion mass range. All precursor ions in the precursor ion mass selection window are fragmented and all of the product ions of all of the precursor ions in the precursor ion mass selection window are mass analyzed.

The precursor ion mass selection window used to scan the mass range can be very narrow so that the likelihood of multiple precursors within the window is small. This type of DIA method is called, for example, MS/MS$^{ALL}$. In an MS/MS$^{ALL}$ method, a precursor ion mass selection window of about 1 amu is scanned or stepped across an entire mass range. A product ion spectrum is produced for each 1 amu precursor mass window. The time it takes to analyze or scan the entire mass range once is referred to as one scan cycle. Scanning a narrow precursor ion mass selection window across a wide precursor ion mass range during each cycle, however, is not practical for some instruments and experiments.

As a result, a larger precursor ion mass selection window, or selection window with a greater width, is stepped across the entire precursor mass range. This type of DIA method is called, for example, SWATH acquisition. In a SWATH acquisition, the precursor ion mass selection window stepped across the precursor mass range in each cycle may have a width of 5-25 amu, or even larger. Like the MS/MS$^{ALL}$ method, all the precursor ions in each precursor ion mass selection window are fragmented, and all of the product ions of all of the precursor ions in each mass selection window are mass analyzed.

SUMMARY

A system, method, and computer program product are disclosed for identifying neutral mass values of at least one molecule in mass spectrometry (MS), in accordance with various embodiments. The system includes an ion source device, a mass spectrometer, and a processor.

The ion source device ionizes at least one molecule of a sample, producing an ion beam. The mass spectrometer selects an m/z range of ions of the ion beam using a mass filter. The mass spectrometer mass analyzes the m/z range using a mass analyzer, producing a mass spectrum.

The processor receives a range of N sequential charge states. The processor creates a copy of the mass spectrum for each of the N charge states, producing N m/z spectra. The processor converts each spectrum of the N spectra to a neutral mass mass spectrum using a different charge state of the N charge states, producing N neutral mass mass spectra. The processor aligns the N neutral mass mass spectra by neutral mass. Finally, when two or more spectra of the N neutral mass mass spectra corresponding to two or more different and sequential charge states include a neutral mass peak above a predetermined intensity threshold at a neutral mass value within a predetermined neutral mass tolerance, the processor identifies the neutral mass value as a neutral mass of the at least one molecule.

These and other features of the applicant's teachings are set forth herein.

BRIEF DESCRIPTION OF THE DRAWINGS AND APPENDICES

The skilled artisan will understand that the drawings, described below, are for illustration purposes only. The drawings are not intended to limit the scope of the present teachings in any way.

Figure 1:
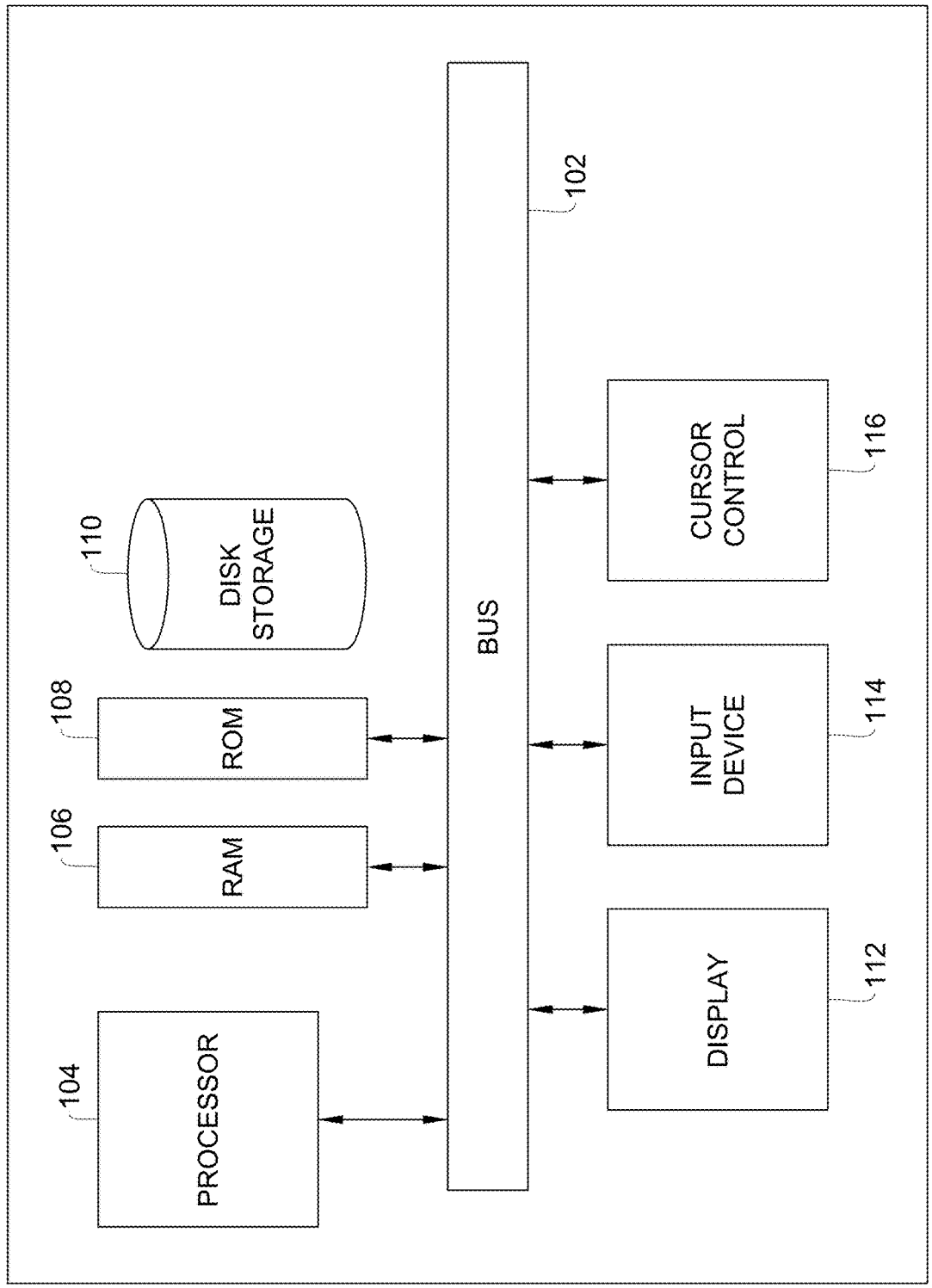
FIG. 1 is a block diagram that illustrates a computer system, upon which embodiments of the present teachings may be implemented.

Appendix 1 is an exemplary presentation describing plots from systems and methods for identifying MW values of at least one molecule in ESI-MS, in accordance with various embodiments.

Appendix 2 is an exemplary description of systems and methods for identifying MW values of at least one molecule in ESI-MS, in accordance with various embodiments.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random-access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively, hard-wired circuitry may be used in place of or in combination with software instructions to implement the present teachings. Thus, implementations of the present teachings are not limited to any specific combination of hardware circuitry and software.

In various embodiments, computer system 100 can be connected to one or more other computer systems, like computer system 100, across a network to form a networked system. The network can include a private network or a public network such as the Internet. In the networked system, one or more computer systems can store and serve the data to other computer systems. The one or more computer systems that store and serve the data can be referred to as servers or the cloud, in a cloud computing scenario. The one or more computer systems can include one or more web servers, for example. The other computer systems that send and receive data to and from the servers or the cloud can be referred to as client or cloud devices, for example.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media or computer program products include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Converting M/Z Values Using a Range of Charge States

Embodiments of systems and methods for identifying MW values of at least one molecule in MS are provided herein, which includes the accompanying Appendix 1 and Appendix 2. In this detailed description, for purposes of explanation, numerous specific details are set forth to provide a thorough understanding of embodiments of the present invention. One skilled in the art will appreciate, however, that embodiments of the present invention may be practiced without these specific details. In other instances, structures and devices are shown in block diagram form. Furthermore, one skilled in the art can readily appreciate that the specific sequences in which methods are presented and performed are illustrative and it is contemplated that the sequences can be varied and remain within the spirit and scope of embodiments of the present invention.

Appendix 1 is an exemplary presentation describing plots from systems and methods for identifying MW values of at least one molecule in ESI-MS, in accordance with various embodiments.

Appendix 2 is an exemplary description of systems and methods for identifying MW values of at least one molecule in ESI-MS, in accordance with various embodiments.

As described above, both quantitative and qualitative analyses of larger molecules by ESI-MS spreads a single chemical form over many sequential charge states. The presence of isotopes and adducts further complicates the situation. The different charge states for these forms can partially or more significantly overlap in the mass-to-charge ratio (m/z) dimension.

Spectral peak-finding algorithms process each peak or at least each isotope cluster as an independent entity and do not make use of the fact that there is additional information available in the related charge states. As a result, confirming a peak currently involves following an arduous manual process. First, a mass in MW is selected. Then the mass spectrum is interrogated to determine if there are m/z peaks for the selected molecular weight at many different and sequential charge states. Typically, this is very difficult to determine without constantly zooming in and out of the mass spectrum. Consequently, it is a time-consuming process.

FIGS. 2-5 show how difficult it can be to confirm the presence of an MW mass peak of a large molecule using conventional mass spectrometry methods and systems. As a result, additional systems and methods are needed to confirm the presence of an MW mass peak of a large molecule when such a peak is spread over many sequential charge states by ESI-MS.

In various embodiments, a sequential range of two or more charge states is selected. The intensity versus m/z values of a mass spectrum of a large molecule are copied for each charge state of the two or more charge states. Each copy of the intensity versus m/z values of the mass spectrum is then converted to intensity versus MW using a different charge state of the two or more charge states. Finally, the two or more intensity versus MW converted spectra are aligned by MW to confirm the presence of an MW mass peak of the large molecule.

One of ordinary skill in the art understands that converting m/z values to MWs is often referred to as multiplying the m/z values by the charge. However, more specifically, the m/z values are converted by multiplying them by the charge state and subtracting any mass of the charge agent. In other words, the charge acquired by an ion can also include a mass. As a result, any time converting m/z values to MWs is herein referred to as multiplying the m/z value by the charge or charge state, it is also understood that this calculation involves subtracting any mass of the charge from the m/z value.

In various embodiments, alignment of the two or more intensity versus molecular weight converted spectra can provide more details about the molecule and can more confidently handle low signal-to-noise (S/N) measurements. A three-dimensional (3D) heat map is one method of aligning the spectral signal across charge states.

Figure 6:
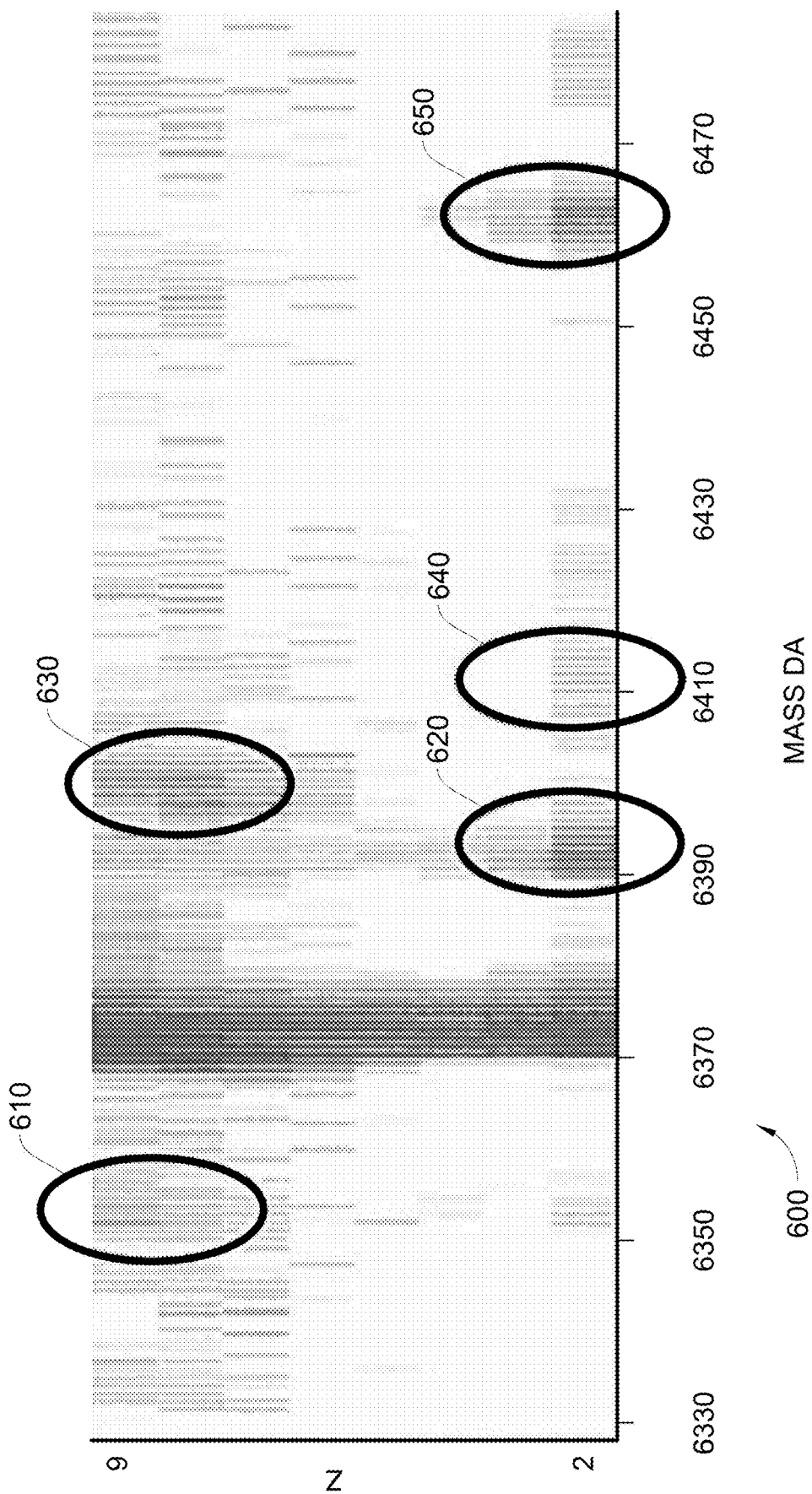
FIG. 6 is an exemplary plot of a three-dimensional (3D) heat map showing eight copies of a single spectrum of an oligonucleotide that have each been converted to an MW spectrum by a different charge state of eight sequential charge states and aligned by MW, in accordance with various embodiments.

FIG. 6 is an exemplary plot 600 of a 3D heat map showing eight copies of a single spectrum of an oligonucleotide that have each been converted to an MW spectrum by a different charge state of eight sequential charge states and aligned by MW, in accordance with various embodiments. In FIG. 6, the x-axis is MW, the y-axis is the charge state used to convert the spectrum, and the increasing darkness of each line in each charge state represents the spectral intensity. It can be seen immediately that the MW near 6370 Da corresponds to a component present in the spectrum since the same MW appears for many charge states (and these charge states are adjacent and not randomly distributed). In other words, the alignment of intensities near 6370 Da for all eight charge states provides confidence that this MW is correct.

Further, clusters 610, 620, 630, 640, and 650 are related to this main component (hydrogen replaced by sodium or potassium, loss of water, desaturation, etc.). If any one charge state for these other forms is analyzed in isolation in the m/z spectrum it is unclear at lower S/N whether the putative form is related to the main component or not. However, using spectra converted to MW in FIG. 6 makes this much clearer since, again, these forms are present in at least a few adjacent charge states and so the MW is likely correct. In other words, since each of forms 610, 620, 630, 640, and 650 relate to the main component near 6370 Da, they boost the confidence in the main component near 6370 Da. Further, since forms 610, 620, 630, and 650 include intensities in two or more sequential charge states, confidence in each of these forms is increased.

In FIG. 6, eight copies of the same m/z values are multiplied by eight different charge states. The intensities of these eight copies are then aligned by MW. In various embodiments, the intensities of these different charge states can also be normalized. For example, the intensities can be normalized to the base peak (highest intensity) in each isotope cluster.

Consider form 650 in FIG. 6. The intensities in each charge state of form 650 are not normalized. As a result, it looks like a charge state of +2 is favored over a charge state of +3 or +4. This is because the intensities in a charge state of +2 are larger (darker lines) than the intensities in the other two charge states. However, each isotopic pattern (lines separated by 1 Da) of each charge state can be normalized to a base peak. In that case, the isotopic patterns in each of the three charge states of form 650 would have similar intensities (darkness). That would make each of the three isotopic patterns have roughly the same intensity, further confirming that sequential charge states for the same form are aligned.

Figure 7:
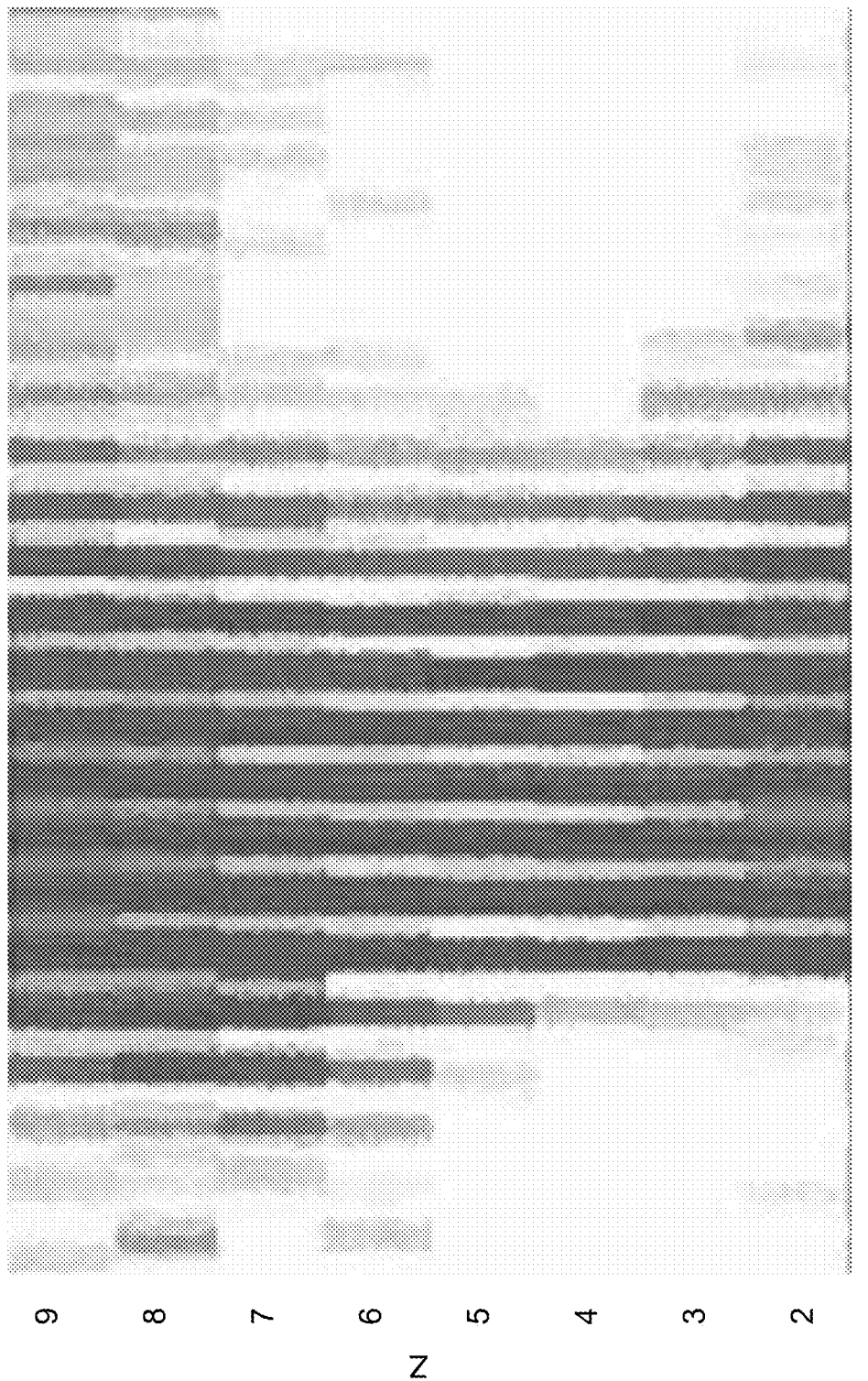
FIG. 7 is an exemplary section of the 3D heat map of FIG. 6 showing the region around 6370 Da in more detail, in accordance with various embodiments.

FIG. 7 is an exemplary section 700 of the 3D heat map of FIG. 6 showing the region around 6370 Da in more detail, in accordance with various embodiments. FIG. 7 shows more clearly the isotope series near 6370 Da. In other words, the lines (one Da apart) near 6370 Da represent an MW mass peak and its isotopic components. For the lower charge states (bottom of the figure), a component of the isotope series with a given MW is present just before 6370 Da. However, at higher charge states (top of the figure) the MW of the component appears to have shifted 2 Da lower. Even at lower charge states, the peak is strong and it is not simply that the first isotopes are small and not visible. There seems to be a real shift (probably loss of two hydrogens)—so the higher charge states probably have a mixture of the original and shifted forms.

By examining any one of the higher charge states in isolation this shift would be almost impossible to detect— the peak would appear to be a single component with the lower MW. Conventional spectral deconvolution algorithms can, at best, deconvolve this to a single broader isotope series making it much more difficult to discover that there are two different species present.

A 3D heat map is just one method of visualizing the alignment of intensity versus MW spectra converted using different sequential charge states. In various alternative embodiments, two or more intensity versus MW spectra converted using different sequential charge states are plotted on top of each other. In other words, the two or more intensity versus MW spectra are overlaid in the same plot where the intensity is plotted as a percentage of a base peak.

Figure 2:
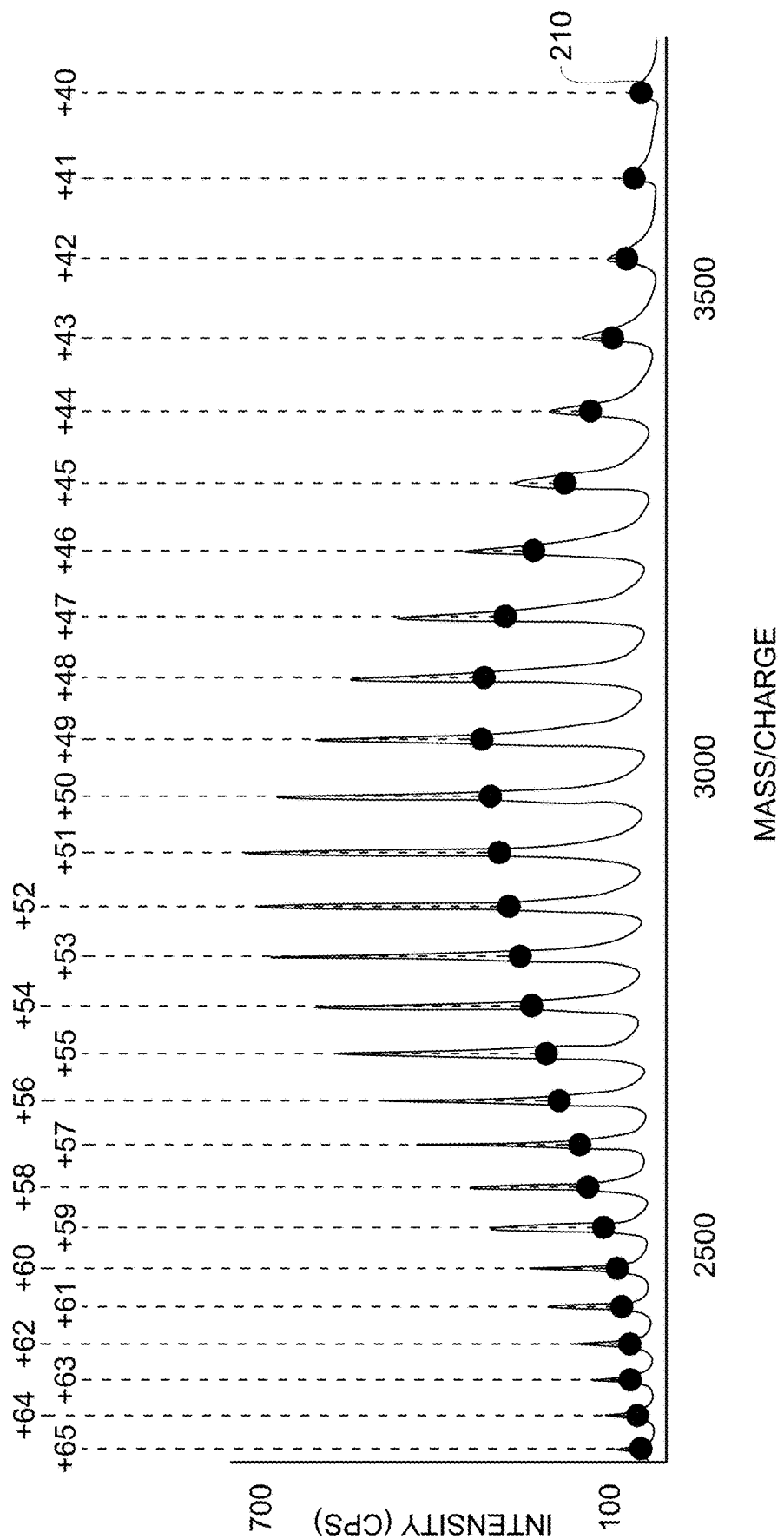
FIG. 2 is an exemplary plot of a mass spectrum of a large molecule (an antibody) showing the location in the m/z dimension of a selected molecular weight (MW) mass at different charge states as displayed by conventional mass spectrometer software.
Figure 8:
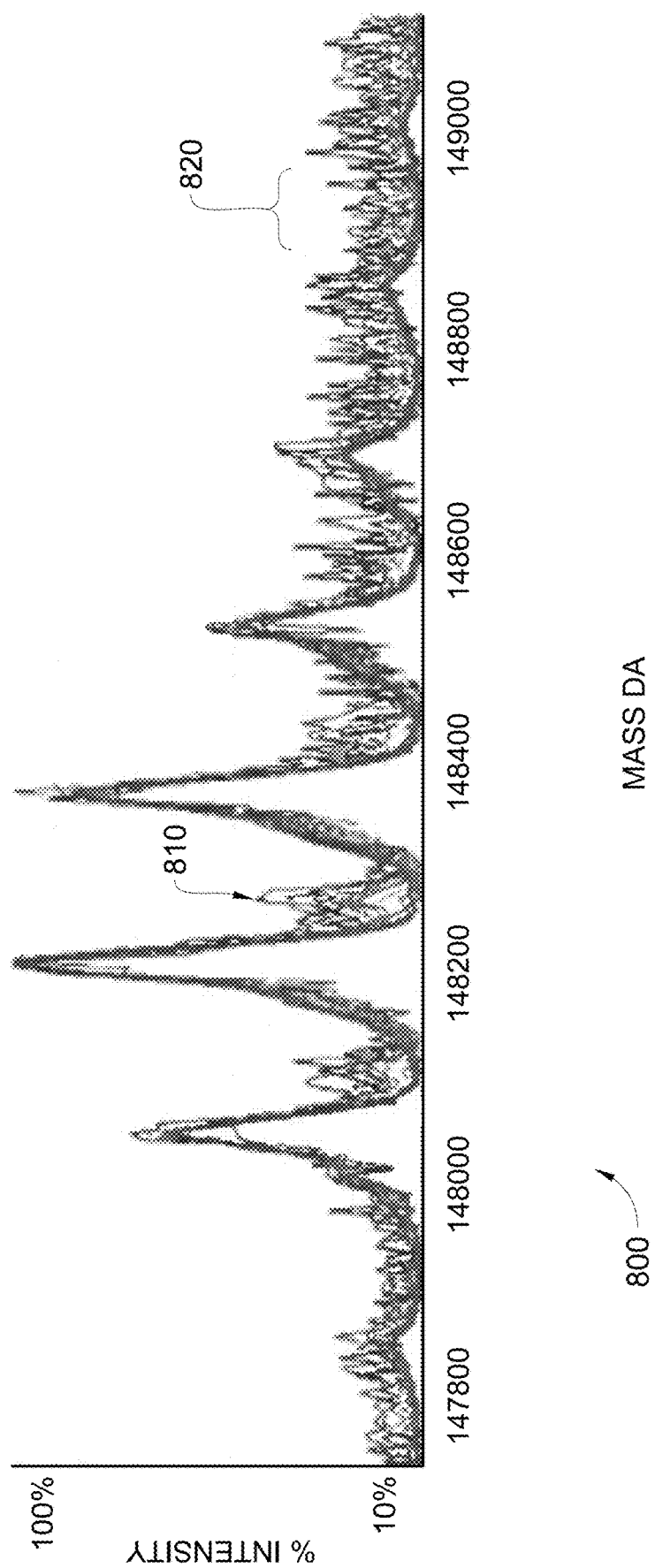
FIG. 8 is an exemplary plot of 21 overlaid intensity versus MW spectra converted using 21 sequential charge states (+40 to +60) from the m/z spectrum of the antibody shown in FIG. 2, in accordance with various embodiments.

FIG. 8 is an exemplary plot 800 of 21 overlaid intensity versus MW spectra converted using 21 sequential charge states (+40 to +60) from the m/z spectrum of the antibody shown in FIG. 2, in accordance with various embodiments. Recall that the selected MW mass in FIG. 2 is 148,274 Da.

Also, recall that it was shown using FIGS. 2-5 how difficult it can be to confirm the presence of MW mass 148,274 Da using conventional methods.

In contrast, FIG. 8 shows how aligning overlaid intensity versus MW spectra in the same plot makes it immediately clear that for a reasonable number of charge states there is evidence for a peak near 148,274 Da. More specifically, the alignment of overlapping peaks 810 for a number of charge states at 148,274 Da confirm the presence of a real peak at 148,274 Da.

Overlapping peaks 810 are aligned in that they have a similar shape near 148,274 Da. Compare peaks 810 with peaks in the region 820, for example. There is no discernable alignment of the peaks in the region 820.

In various embodiments, overlaid intensity versus MW spectra converted using different sequential charge states are plotted automatically and displayed to a user. This allows a user to more easily confirm the presence of MW mass peaks than conventional methods. As shown in FIGS. 2-5 and as described above, the confirmation of the presence of MW mass peaks using conventional methods currently involves a large amount of manual zooming and requires users to remember peak shapes so that they can be compared at different charge states.

In various embodiments, the presence of an MW mass is further confirmed by using data from overlaid intensity versus MW spectra to further express the intensity of a selected MW mass as a function of charge state. For example, the data from the plot in FIG. 8 can be used to express the intensity of MW mass 148,274 Da as a function of charge state.

Figure 9:
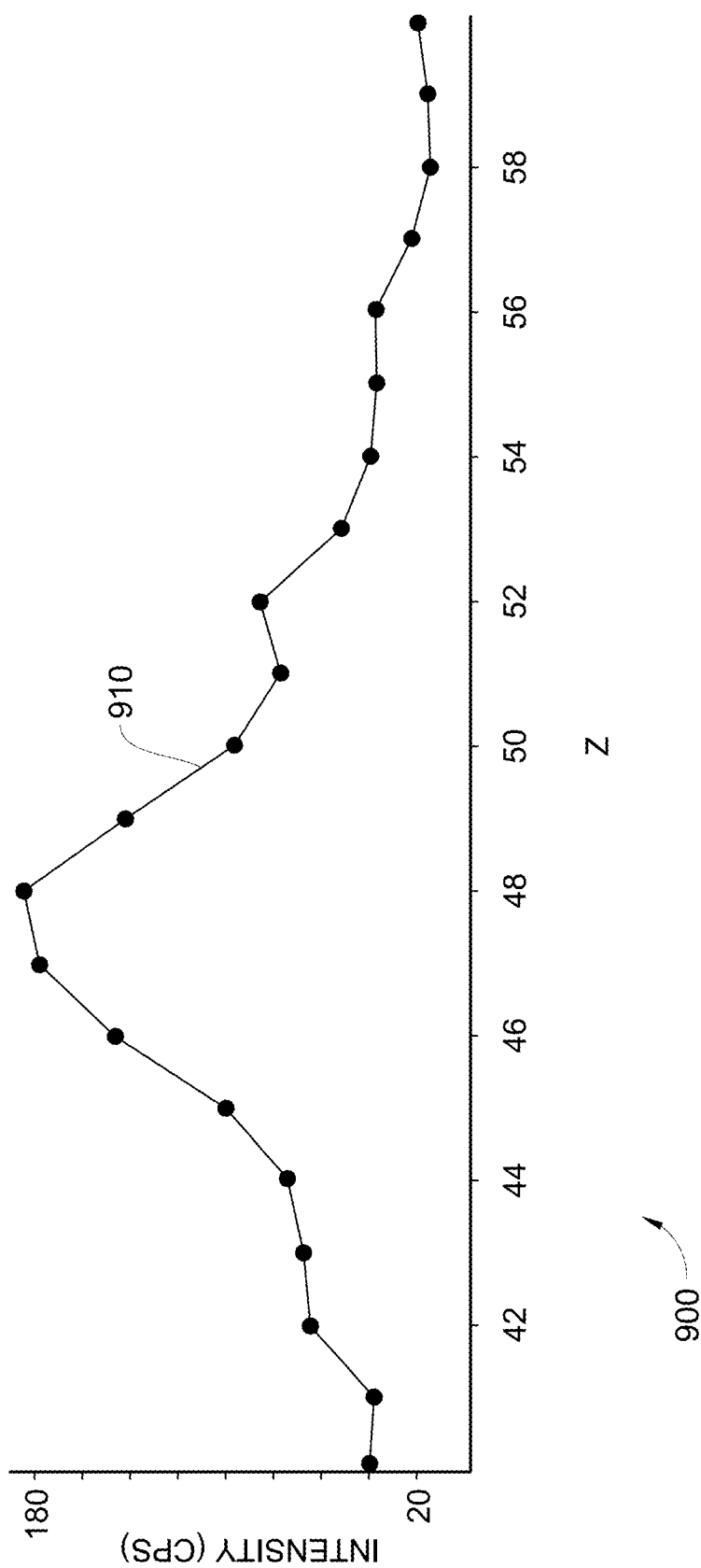
FIG. 9 is an exemplary plot of the MW range near 148,274 Da versus 21 different charge states using the data from the plot of FIG. 8, in accordance with various embodiments.

FIG. 9 is an exemplary plot 900 of the MW range near 148,274 Da versus 21 different charge states using the data from the plot of FIG. 8, in accordance with various embodiments. FIG. 9 shows that the intensity near 148,274 Da varies relatively smoothly with each increasing sequential charge state. In other words, fitted line or function 910 shows that the response is consistent between adjacent charge states. There is not, for example, a nonzero intensity in every second charge state only making the MW a factor or two different. Using a 3D heat map, like the one shown in FIG. 6 similarly makes it clear that the molecular is present in sequential or adjacent charge states.

Figure 3:
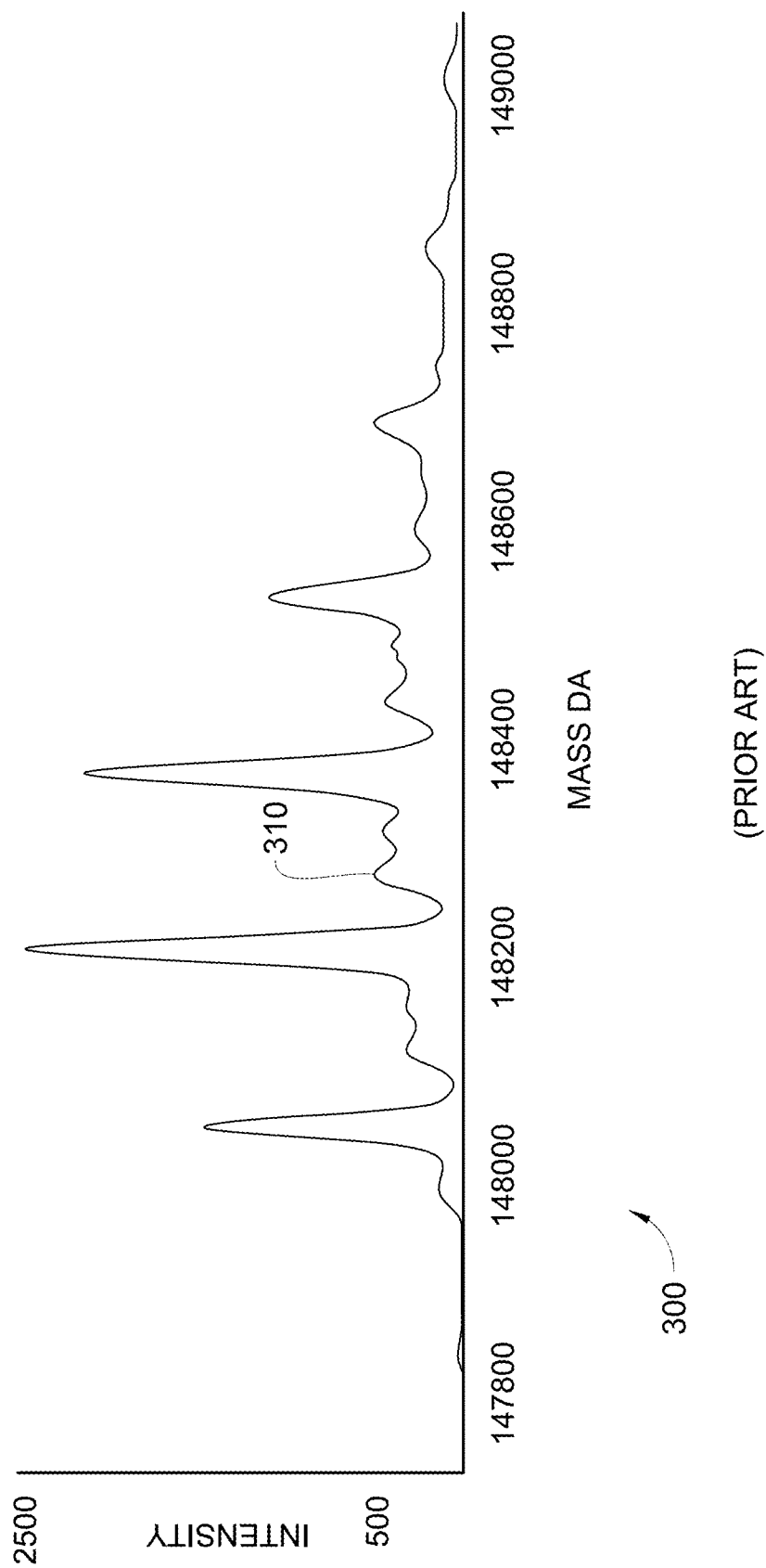
FIG. 3 is an exemplary plot of a reconstructed and deconvoluted MW mass spectrum corresponding to the mass spectrum of FIG. 2 as displayed by conventional mass spectrometer software.
Figure 4:
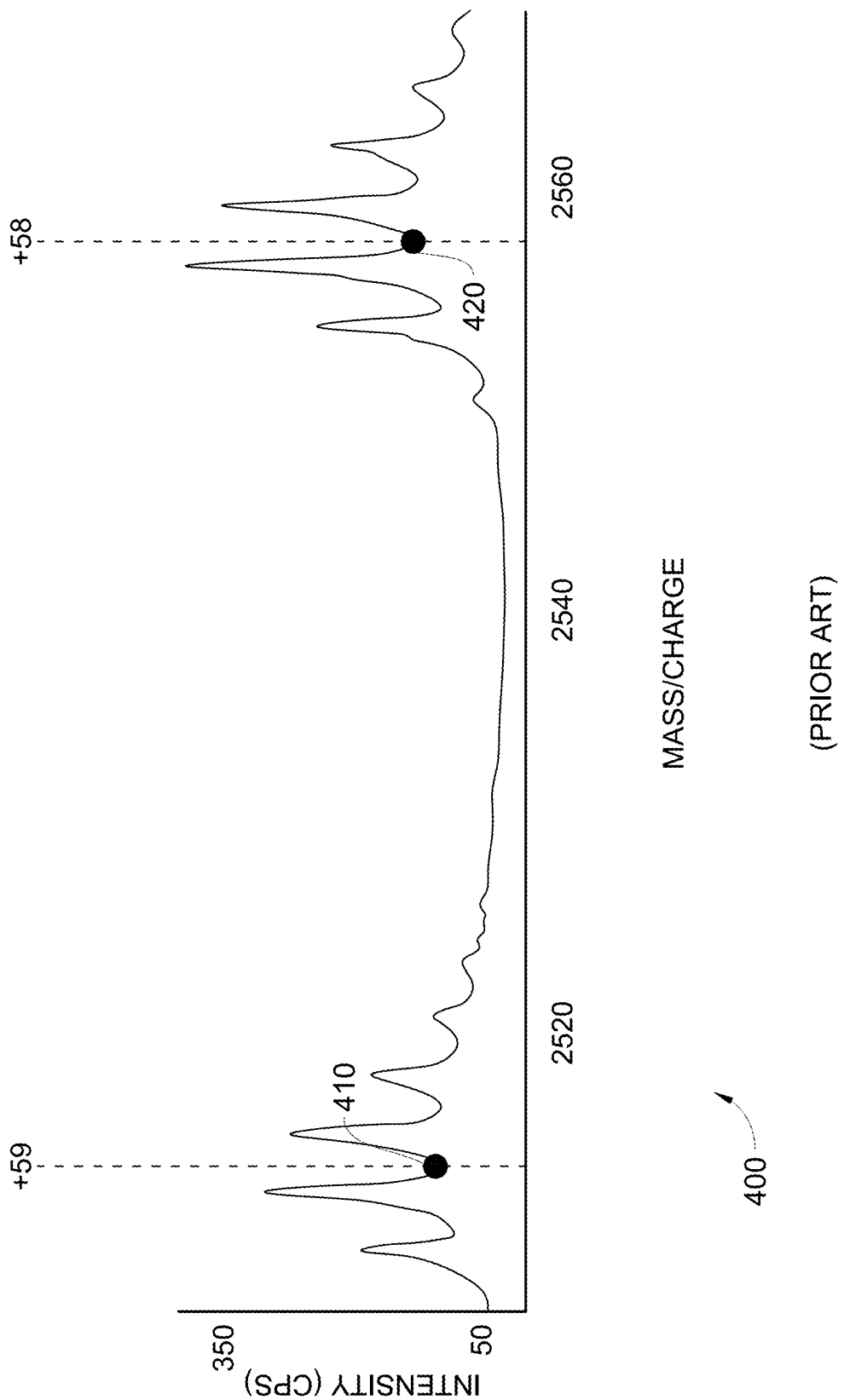
FIG. 4 is an exemplary plot showing the zoomed section of the mass spectrum of FIG. 2 that includes charge states +59 and +58 as displayed by conventional mass spectrometer software.
Figure 5:
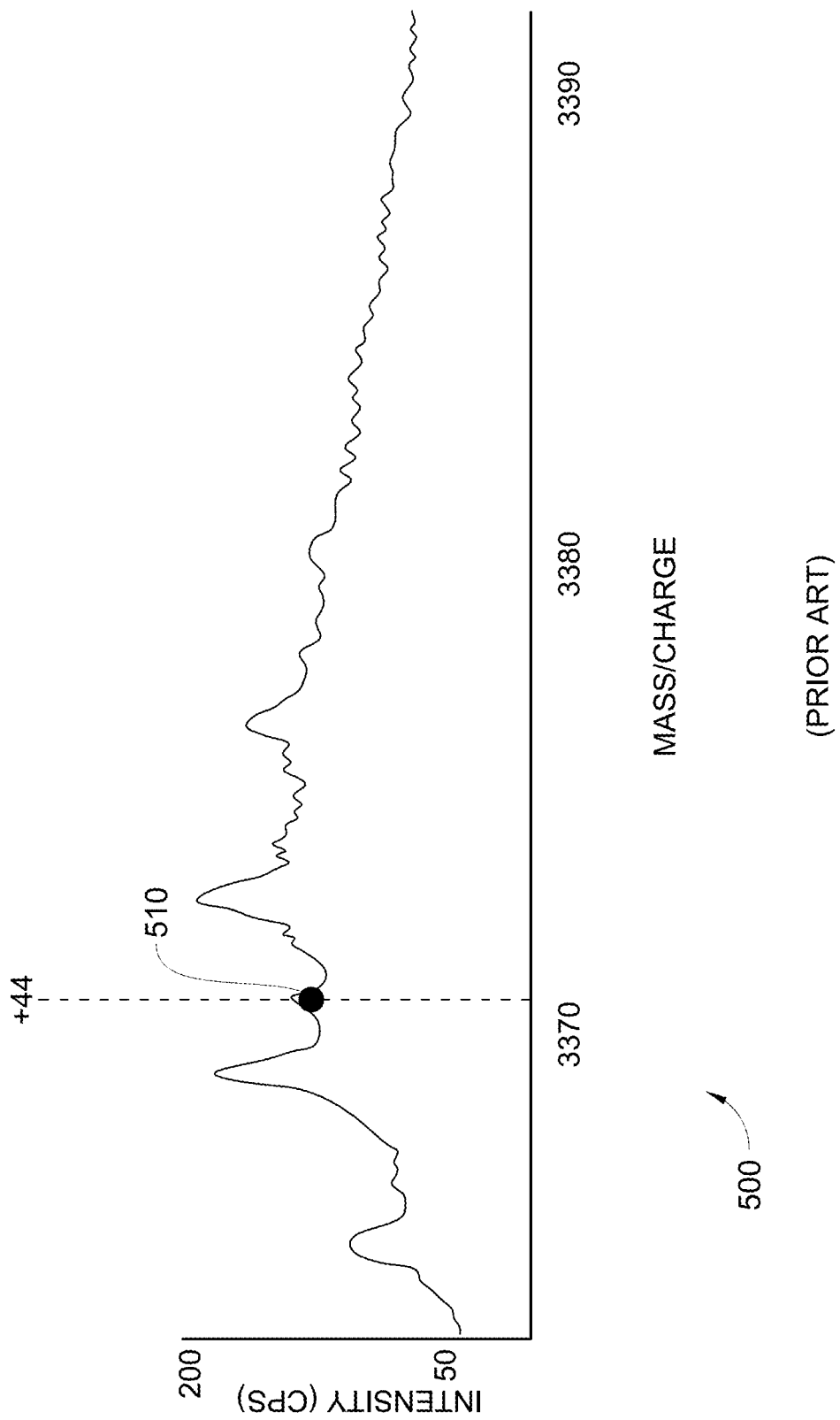
FIG. 5 is an exemplary plot showing the zoomed section of the mass spectrum of FIG. 2 that includes charge state +44 as displayed by conventional mass spectrometer software.
Figure 10:
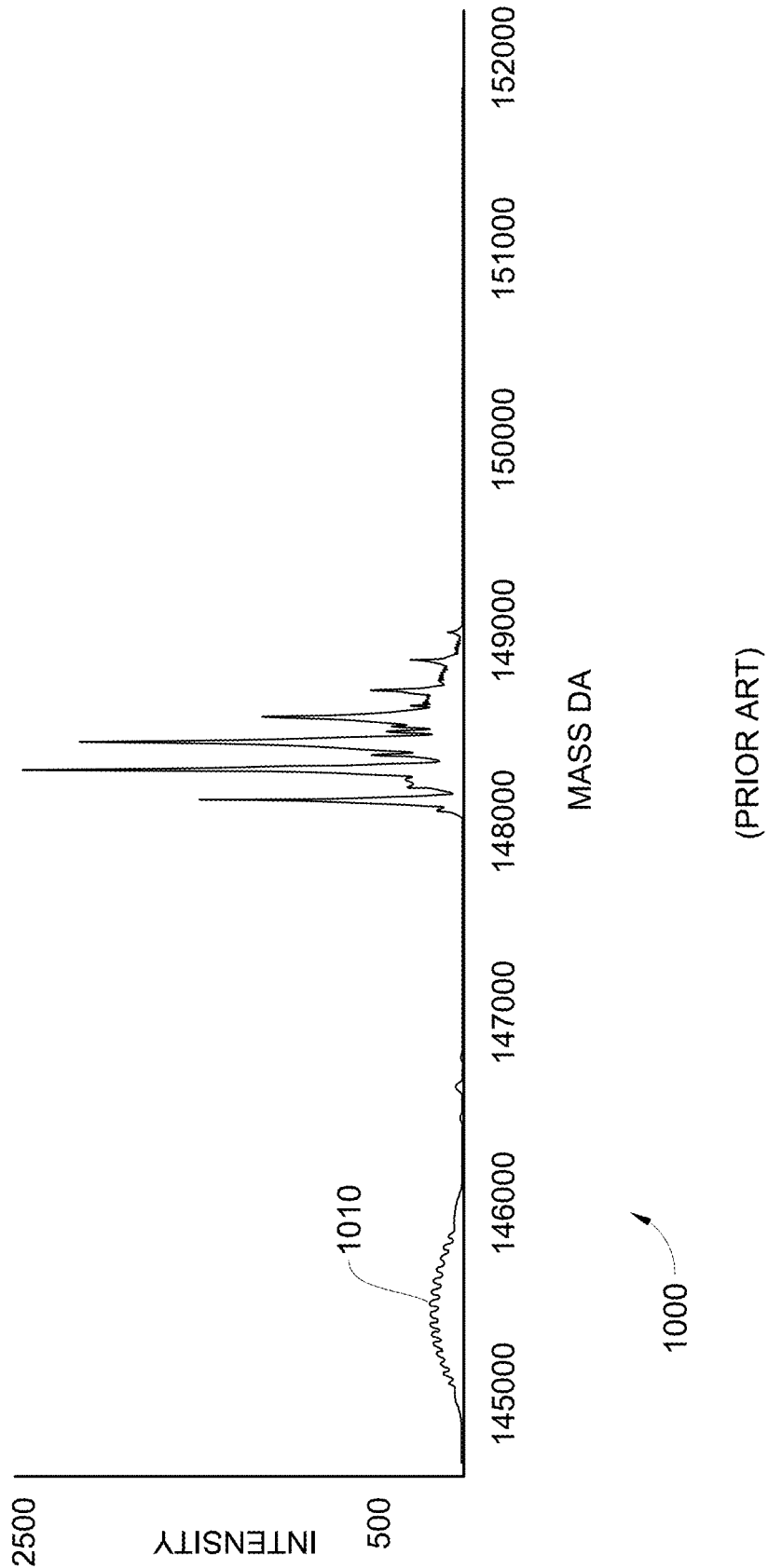
FIG. 10 is an exemplary plot showing an expanded MW range for the same reconstructed and deconvoluted MW mass spectrum shown in FIG. 3.

FIG. 10 is an exemplary plot 1000 showing an expanded MW range for the same reconstructed and deconvoluted MW mass spectrum shown in FIG. 3. Peak 1010 between 145,000 and 146,000 Da is not a real peak. It is an artifact of the conventional reconstruction or deconvolution algorithm. However, this is unclear to many users.

Figure 11:
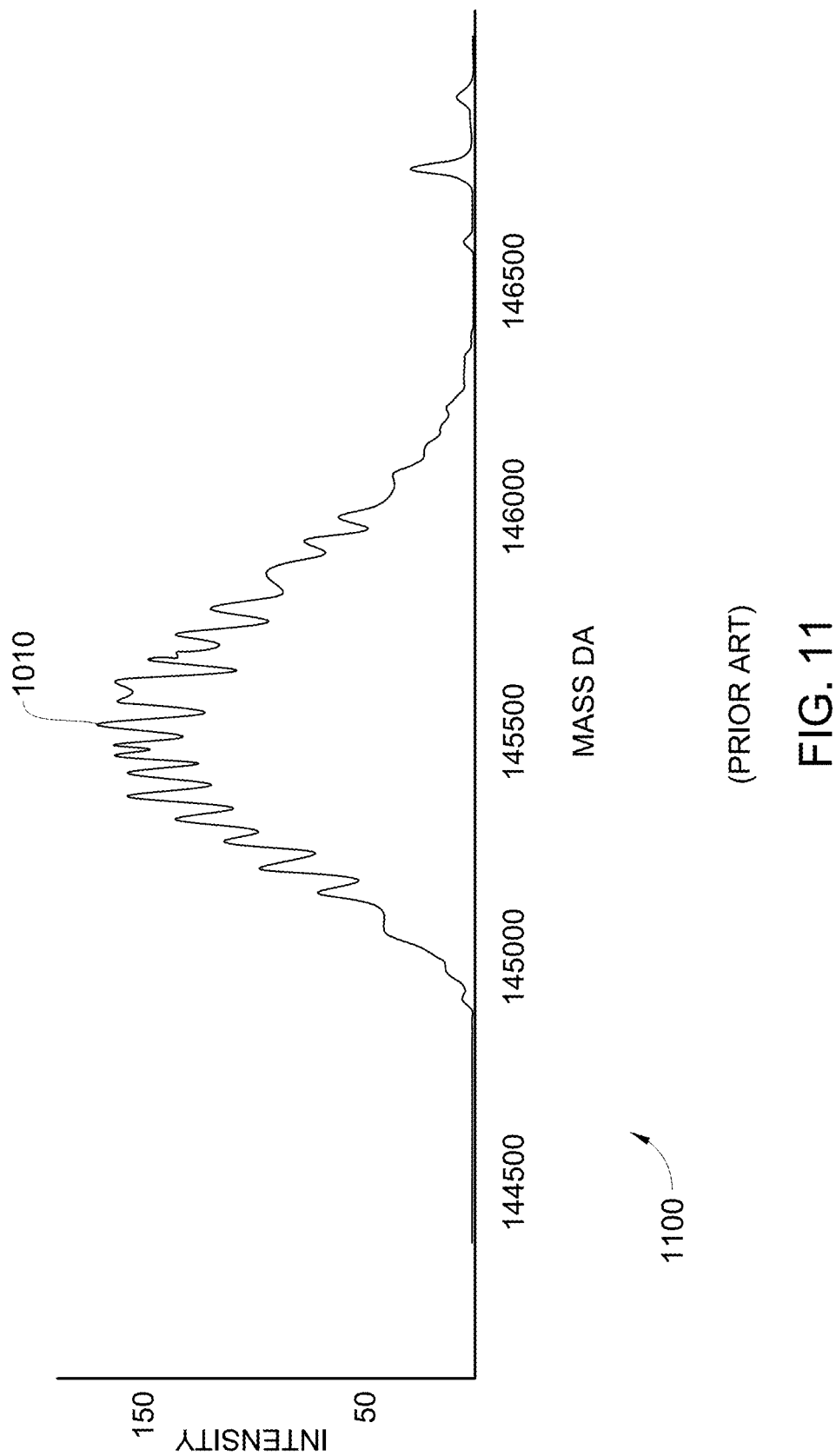
FIG. 11 is an exemplary plot showing the zoomed section between 144,000 and 147,000 Da of the MW mass spectrum of FIG. 10.

FIG. 11 is an exemplary plot 1100 showing the zoomed section between 144,000 and 147,000 Da of the MW mass spectrum of FIG. 10. Peak 1010 between 145,000 and 146,000 Da is more easily seen in FIG. 11. Again, Peak 1010 is not a real peak.

Figure 12:
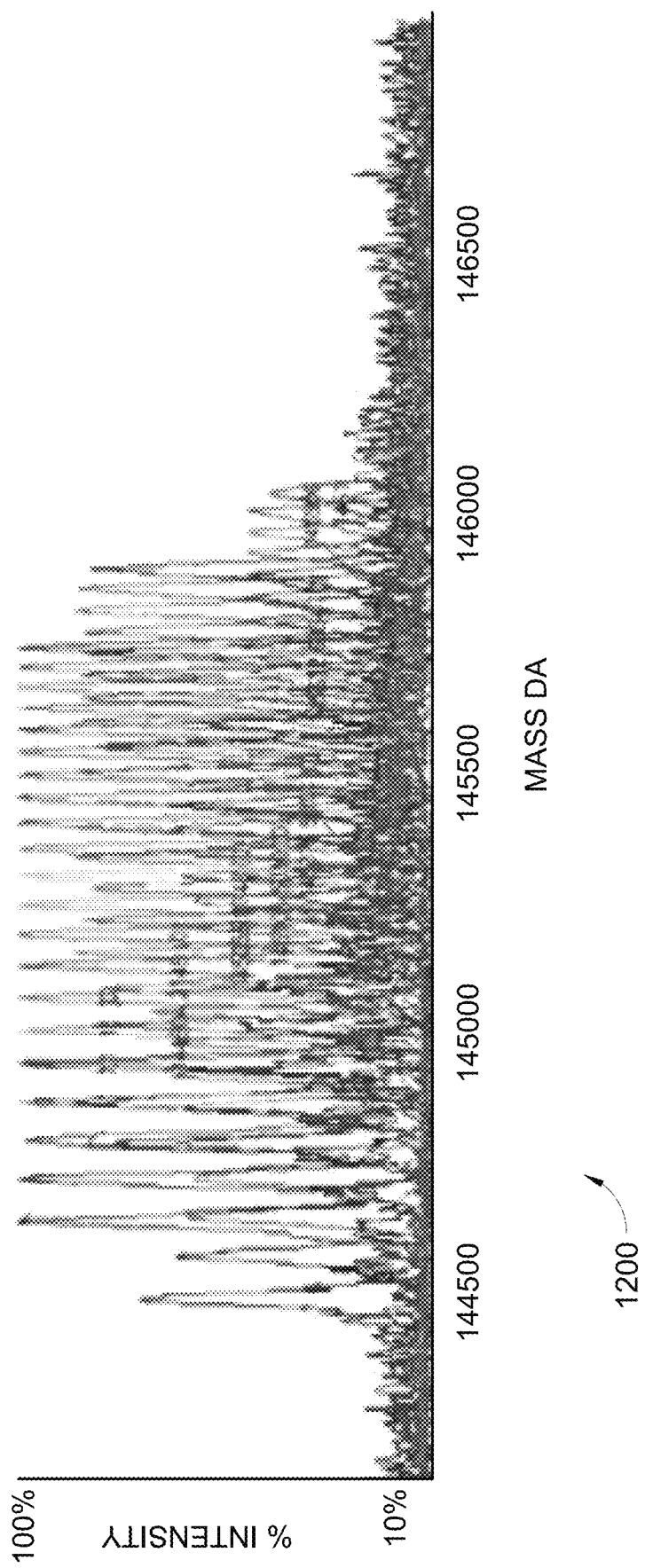
FIG. 12 is an exemplary plot of overlaid intensity versus MW spectra converted using sequential charge states from the m/z spectrum of the antibody shown in FIG. 2 for the region between 144,000 and 147,000 Da, in accordance with various embodiments.

FIG. 12 is an exemplary plot 1200 of overlaid intensity versus MW spectra converted using sequential charge states from the m/z spectrum of the antibody shown in FIG. 2 for the region between 144,000 and 147,000 Da, in accordance with various embodiments. In other words, FIG. 12 shows overlaid intensity versus MW spectra for the peak of FIG. 11. FIG. 12 shows that there is intensity in the region between 144,000 and 147,000 Da. However, it also shows that these charge states are not real because these peaks do not overlap and reinforce one another at a consistent MW. Unlike the overlaid spectra in FIG. 8, the overlaid spectra of FIG. 12 do not form well-aligned peaks. Consequently, it is clear from FIG. 12 that the peak in FIG. 11 is not real.

FIGS. 6, 8, 9, and 12 show how intensity versus MW spectra converted from a single m/z spectrum can be used to visually confirm or refute the presence of an MW mass peak of a large molecule. In various embodiments, this spectral data can also be analyzed automatically confirm or refute the presence of a mass peak.

Figure 13:
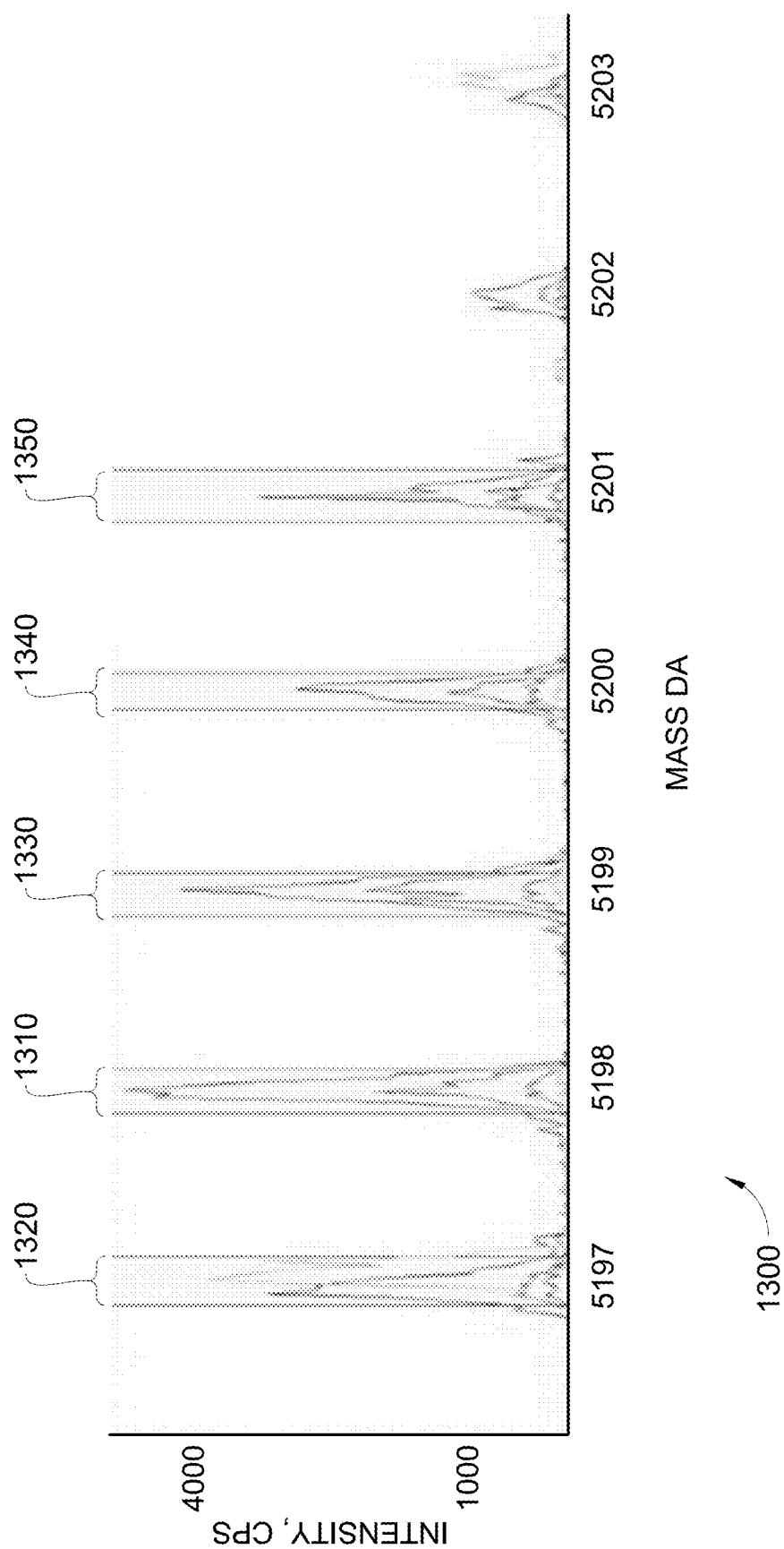
FIG. 13 is an exemplary plot showing real isotopic mass peaks in a zoomed section between 5196.0 and 5203.5 Da of 10 overlaid intensity versus MW spectra converted using 10 sequential charge states from an m/z spectrum of a large molecule, in accordance with various embodiments.

FIG. 13 is an exemplary plot 1300 showing real isotopic mass peaks in a zoomed section between 5196.0 and 5203.5 Da of 10 overlaid intensity versus MW spectra converted using 10 sequential charge states from an m/z spectrum of a large molecule, in accordance with various embodiments. Initially, it is not known whether or not the section between 5196.0 and 5203.5 Da includes real isotopic mass peaks.

In various embodiments, in a first step, the 10 overlaid intensity versus MW spectra are searched for aligned molecular peaks that have an intensity above a certain threshold in two or more sequential charge states. Peaks 1310 in the range 5197.85 to 5198.07 Da are found to have an intensity above a certain threshold in two or more sequential charge states, for example.

In a second step, the mass range on either side of peaks 1310 is then searched for aligned isotopic peaks spaced a multiple of 1 Da from peaks 1310. Peaks 1320, 1330, 1340, and 1350 are found. This step is referred to as mass pattern filtering, for example. Peaks 1320 are found in the range 5196.89 to 5197.13 Da. Peaks 1330 are found in the range 5198.85 to 5199.07 Da. Peaks 1340 are found in the range 5199.89 to 5200.07 Da. Peaks 1350 are found in the range 5200.83 to 5201.10 Da. Note that in FIG. 13 the intensities of each spectrum are not plotted in percent intensity as in FIG. 8. As a result, the aligned peaks of FIG. 13 have different intensities.

Group of peaks 1310 includes the highest intensity peak. In various embodiments, the peak group with the highest intensity peak is selected. Isotopic peaks are found by moving in steps of 1 Da in increasing mass or 1 Da in decreasing mass from the peak group with the highest intensity peak.

In a third step, the percent intensity of each group of isotopic peaks found in the second step is expressed as a function of charge state. The functions of the different groups of isotopic peaks are analyzed and compared. Although performed automatically, this comparison can be shown graphically.

Figure 14:
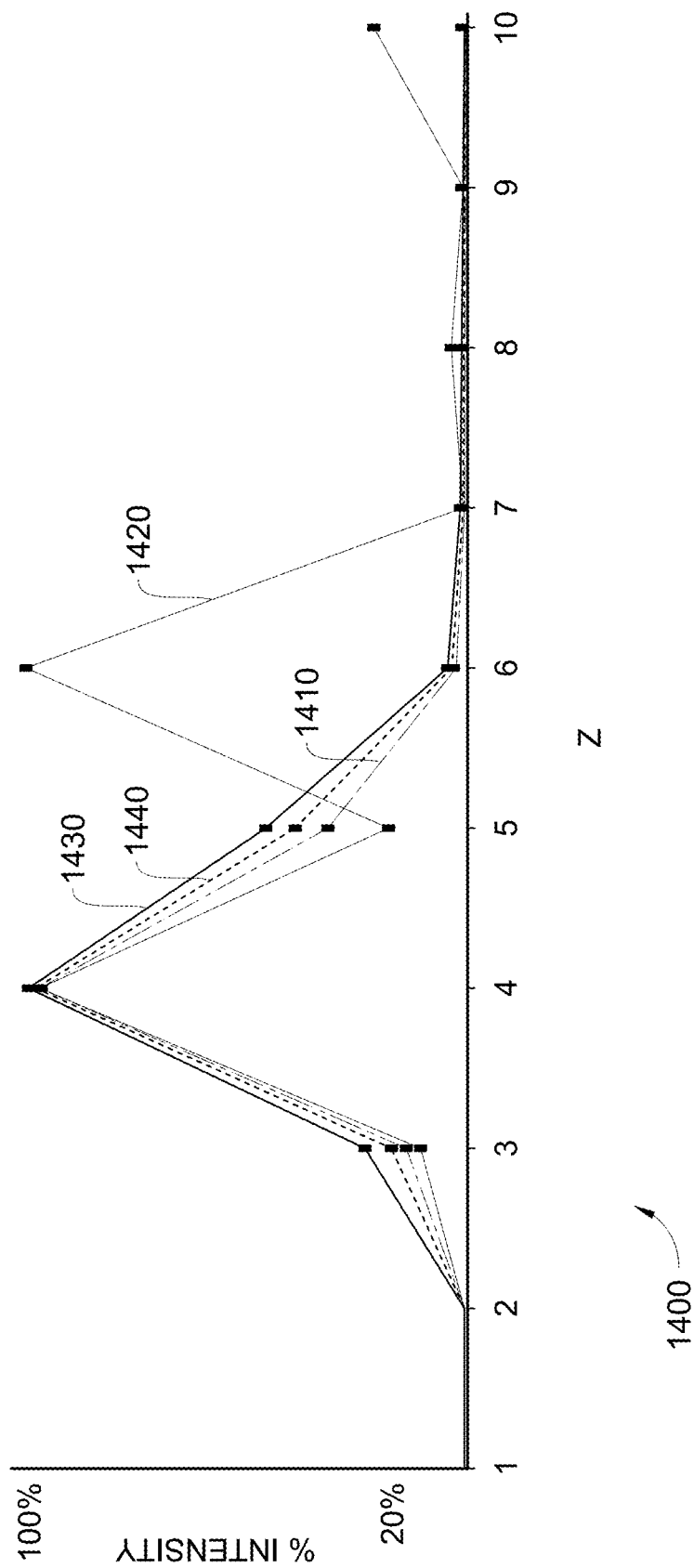
FIG. 14 is an exemplary plot 1400 of intensity versus charge state for the five possible isotopic peak groups found from the data of FIG. 13, in accordance with various embodiments.

FIG. 14 is an exemplary plot 1400 of intensity versus charge state for the five possible isotopic peak groups found from the data of FIG. 13, in accordance with various embodiments. In FIG. 14, line 1410 shows how the percent intensity of both peaks 1310 and 1350 of FIG. 13 vary with charge state. Line 1420 of FIG. 14 shows how the percent intensity of peak 1320 of FIG. 13 varies with charge state. Line 1430 of FIG. 14 shows how the percent intensity of peak 1330 of FIG. 13 varies with charge state. Line 1440 of FIG. 14 shows how the percent intensity of peak 1340 of FIG. 13 varies with charge state.

Lines 1410, 1420, 1430, and 1440 are analyzed for smooth transitions between charges and for similar shapes. Lines 1410, 1430, and 1440 all have a similar shape. They smoothly increase from zero intensity to a maximum and then smoothly decrease to zero over a number of charge states. They are not jumping in intensity between charge states. Mathematically, lines 1410, 1430, and 1440 have no local minima as they increase to and decrease from a maximum. Lines 1410, 1430, and 1440 provide evidence that peaks 1310, 1330, 1340, and 1350 of FIG. 13 comprise a real isotopic pattern in the region between 5196.0 and 5203.5 Da.

Returning to FIG. 14, line 1420 does, however, jump from high intensity to low intensity and then back to high intensity and does not have a shape that is similar to the other lines. In other words, line 1420 does have a single local minimum. As a result, line 1420 corresponding peaks 1320 of FIG. 13 is an outlier. It is likely that the behavior of line 1420 is caused by another compound that produces the same MW when multiplied by the wrong charge state. However, despite line 1420, analysis and comparison of the lines in FIG. 14 confirms that there is a real peak in the region between 5196.0 and 5203.5 Da.

Figure 15:
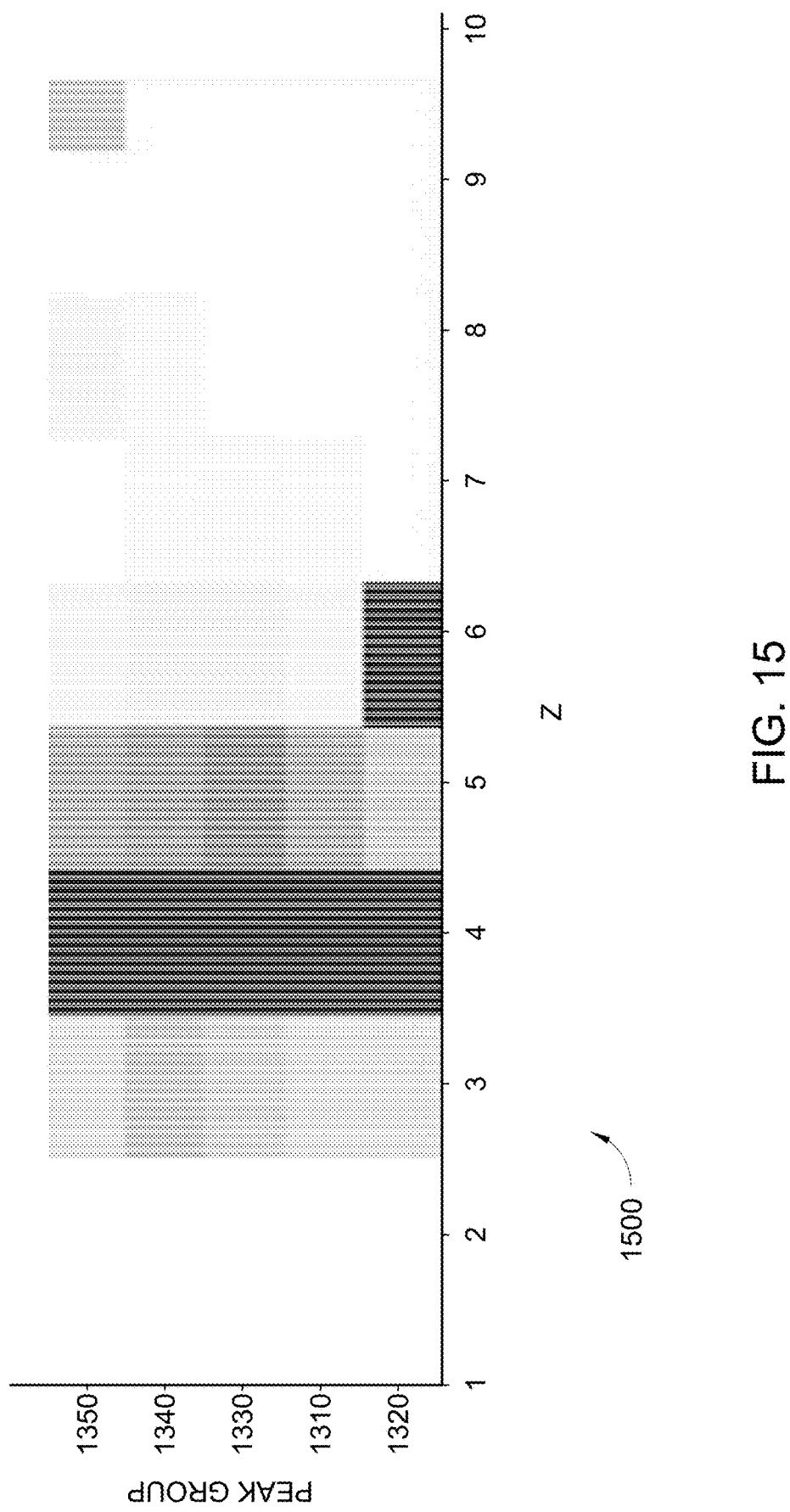
FIG. 15 is an exemplary plot of a 3D heat map of intensity versus charge state for the five possible isotopic peak groups found from the data of FIG. 13, in accordance with various embodiments.

FIG. 15 is an exemplary plot 1500 of a 3D heat map of intensity versus charge state for the five possible isotopic peak groups found from the data of FIG. 13, in accordance with various embodiments. In FIG. 15, the five rows correspond to the five possible isotopic peak groups 1320, 1310, 1330, 1340, and 1350 (from bottom to top) of FIG. 13. The ten columns of FIG. 15 correspond to the ten charge states. The increasing darkness of each square represents increasing intensity.

Like FIG. 14, FIG. 15 shows that peak groups 1310, 1330, 1340, and 1350 all smoothly increase from zero intensity to a maximum and then smoothly decrease to zero over a number of charge states. Also, like FIG. 14, FIG. 15 shows that peak group 1320 is an outlier because it jumps from high intensity to low intensity and then back to high intensity.

Figure 16:
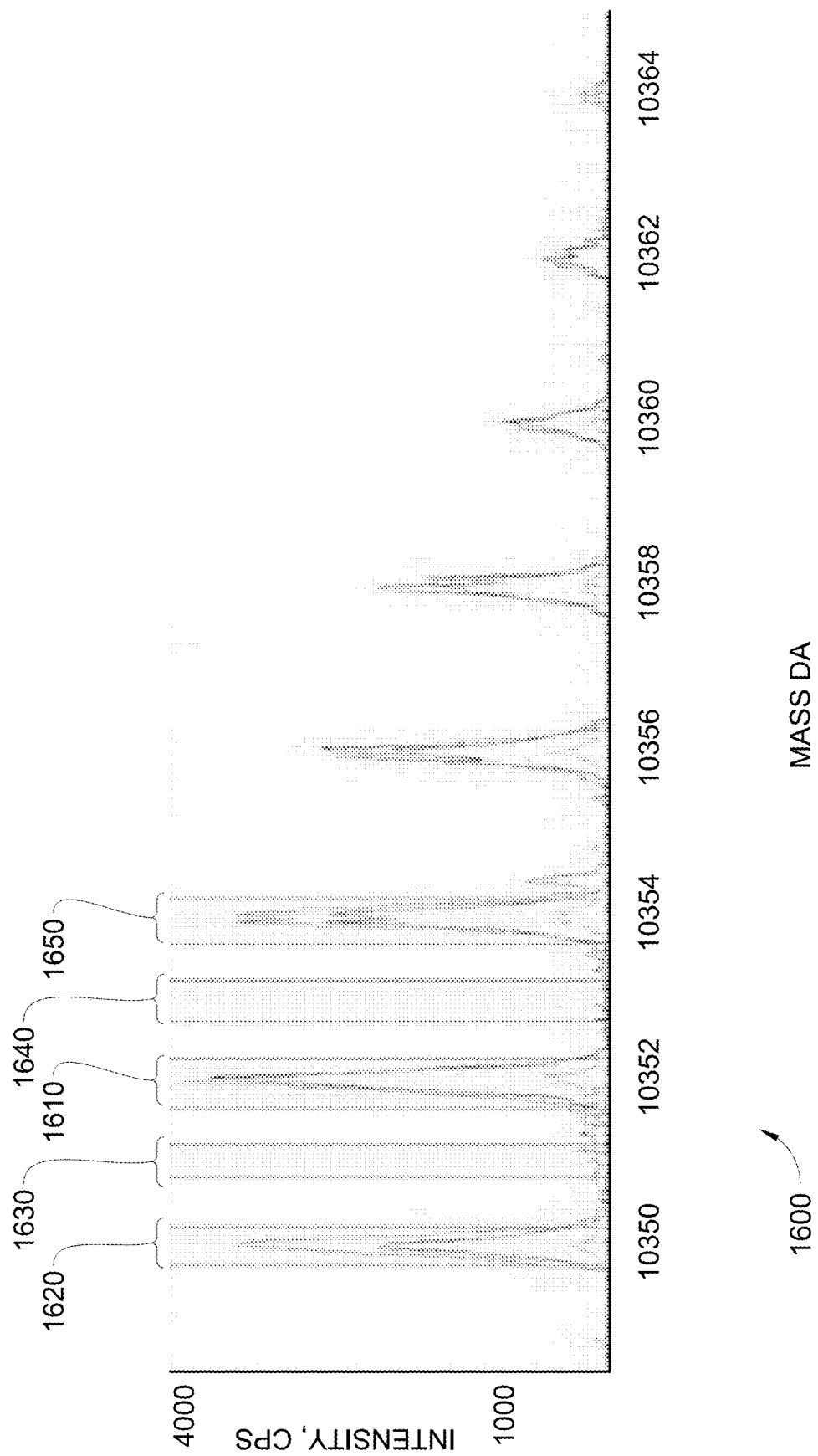
FIG. 16 is an exemplary plot showing peaks that are not real isotopic mass peaks in a zoomed section between 10348 and 10365 Da of 10 overlaid intensity versus MW spectra converted using 10 sequential charge states from an m/z spectrum of a large molecule, in accordance with various embodiments.

FIG. 16 is an exemplary plot 1600 showing peaks that are not real isotopic mass peaks in a zoomed section between 10348 and 10365 Da of 10 overlaid intensity versus MW spectra converted using 10 sequential charge states from an m/z spectrum of a large molecule, in accordance with various embodiments. Initially, it is not known whether or not the section between 10348 and 10365 Da includes real isotopic mass peaks.

Again, in a first step, the 10 overlaid intensity versus MW spectra are searched for aligned molecular peaks that have an intensity above a certain threshold in two or more sequential charge states. Peaks 1610 in the range 10351.64 to 10352.25 Da are found to have an intensity above a certain threshold in two or more sequential charge states, for example.

In a second step, the mass range on either side of peaks 1610 is then searched for aligned isotopic peaks spaced a multiple of 1 Da from peaks 1610. Peaks 1620, 1630, 1640, and 1650 are found. [Peaks 1620 are found in the range 10349.74 to 10350.21 Da. Peaks 1630 are found in the range 10350.80 to 10351.20 Da. Peaks 1640 are found in the range 10352.70 to 10353.20 Da. Peaks 1650 are found in the range 10353.65 to 10354.21 Da.

Group of peaks 1610 includes the highest intensity peak. In various embodiments, the peak group with the highest intensity peak is selected. Isotopic peaks are found by moving in steps of 1 Da in increasing mass or 1 Da decreasing mass from the peak group with the highest intensity peak.

In a third step, the percent intensity of each group of isotopic peaks found in the second step is expressed as a function of charge state. The functions of the different groups of isotopic peaks are analyzed and compared. Although performed automatically, this comparison can again be shown graphically.

Figure 17:
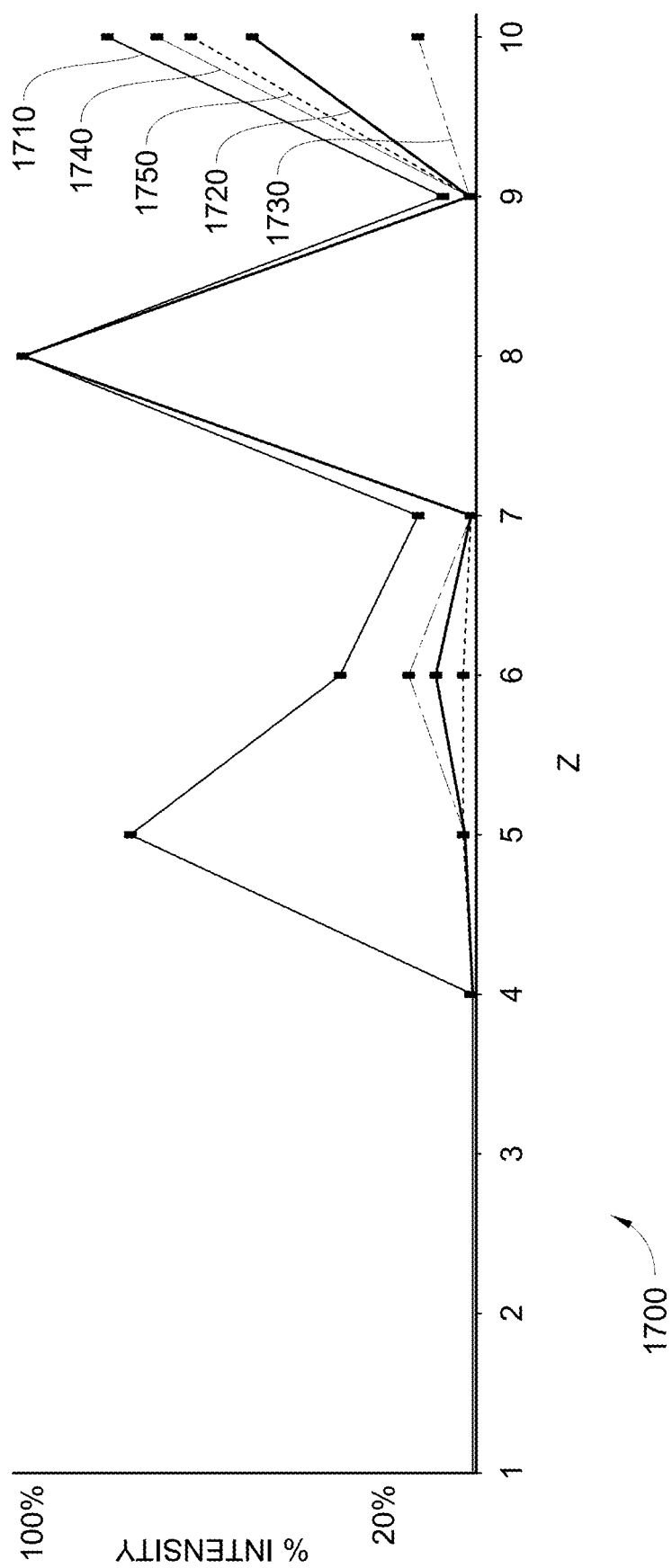
FIG. 17 is an exemplary plot of intensity versus charge state for the five possible isotopic peak groups found from the data of FIG. 16, in accordance with various embodiments.

FIG. 17 is an exemplary plot 1700 of intensity versus charge state for the five possible isotopic peak groups found from the data of FIG. 16, in accordance with various embodiments. In FIG. 17, lines 1710, 1720, 1730, 1740, and 1750 show how the percent intensities of peaks 1610, 1620, 1630, 1640, and 1650 of FIG. 16, respectively, vary with charge state.

Lines 1710, 1720, 1730, 1740, and 1750 are analyzed for smooth transitions between charges and for similar shapes. Lines 1710, 1720, 1730, and 1750 all have a similar shape. Only line 1740 is slightly different and has a large intensity at charge state +5. However, all five lines fail to have smooth transitions between charges. In particular, all five lines decrease from charge state +6 to charge state +7, increase again from charge state +7 to charge state +8, and then decrease from charge state +8 to charge state +9. Most significantly, all lines have zero intensity or have small intensities values at charge states immediately before and after charge state +8, which has the maximum intensity. This up and down pattern of these lines is a clear sign that the isotopic pattern is incorrect and therefore that the MW is not real.

Figure 18:
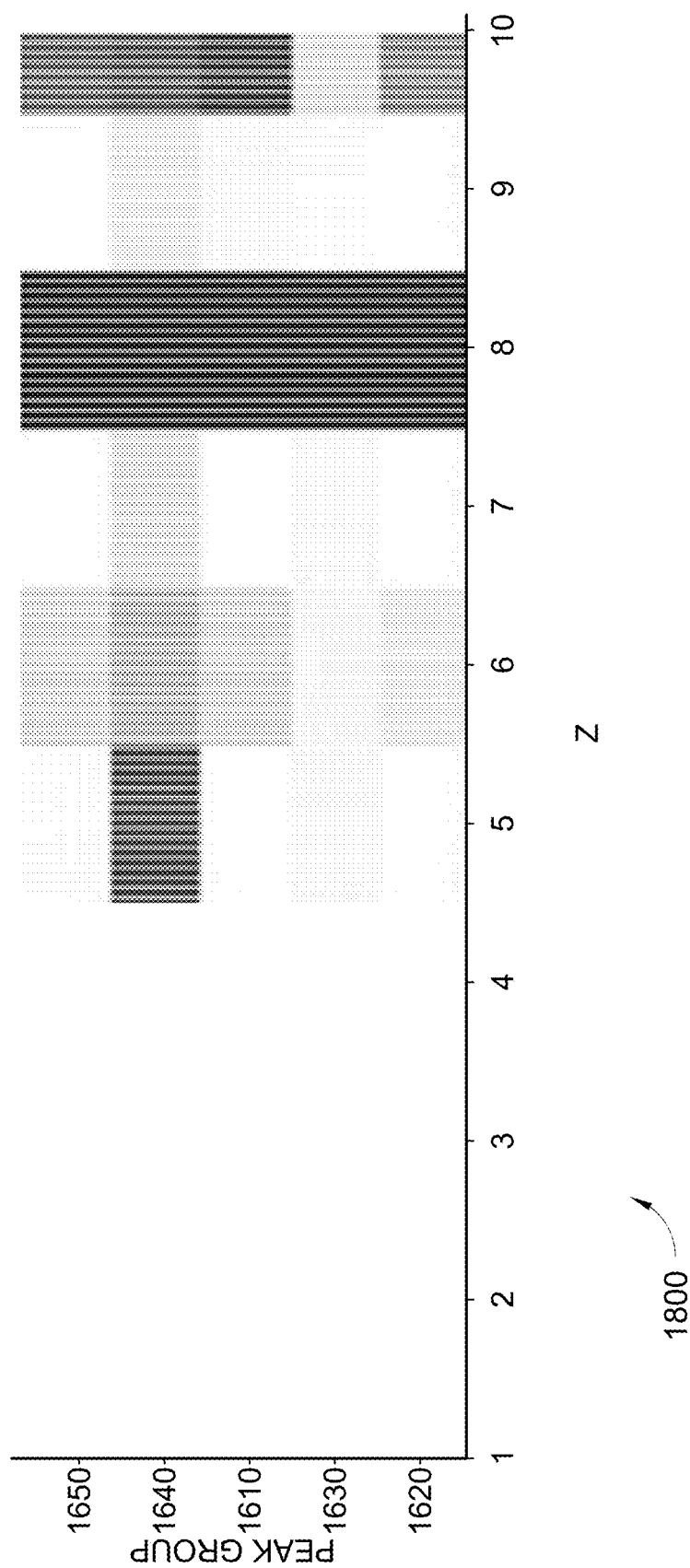
FIG. 18 is an exemplary plot of a 3D heat map of intensity versus charge state for the five possible isotopic peak groups found from the data of FIG. 16, in accordance with various embodiments.

FIG. 18 is an exemplary plot 1800 of a 3D heat map of intensity versus charge state for the five possible isotopic peak groups found from the data of FIG. 16, in accordance with various embodiments. In FIG. 18, the five rows correspond to the five possible isotopic peak groups 1620, 1630, 1610, 1640, and 1650 (from bottom to top) of FIG. 17. The ten columns of FIG. 18 correspond to the ten charge states. The increasing darkness of each square represents increasing intensity.

Like FIG. 17, FIG. 18 shows that peak groups 1620, 1630, 1610, 1640, and 1650 all have intensities that decrease from charge state +6 to charge state +7, increase again from charge state +7 to charge state +8, and then decrease from charge state +8 to charge state +9. As a result, FIG. 18 also shows that the isotopic pattern of FIG. 16 is incorrect.

Figure 19:
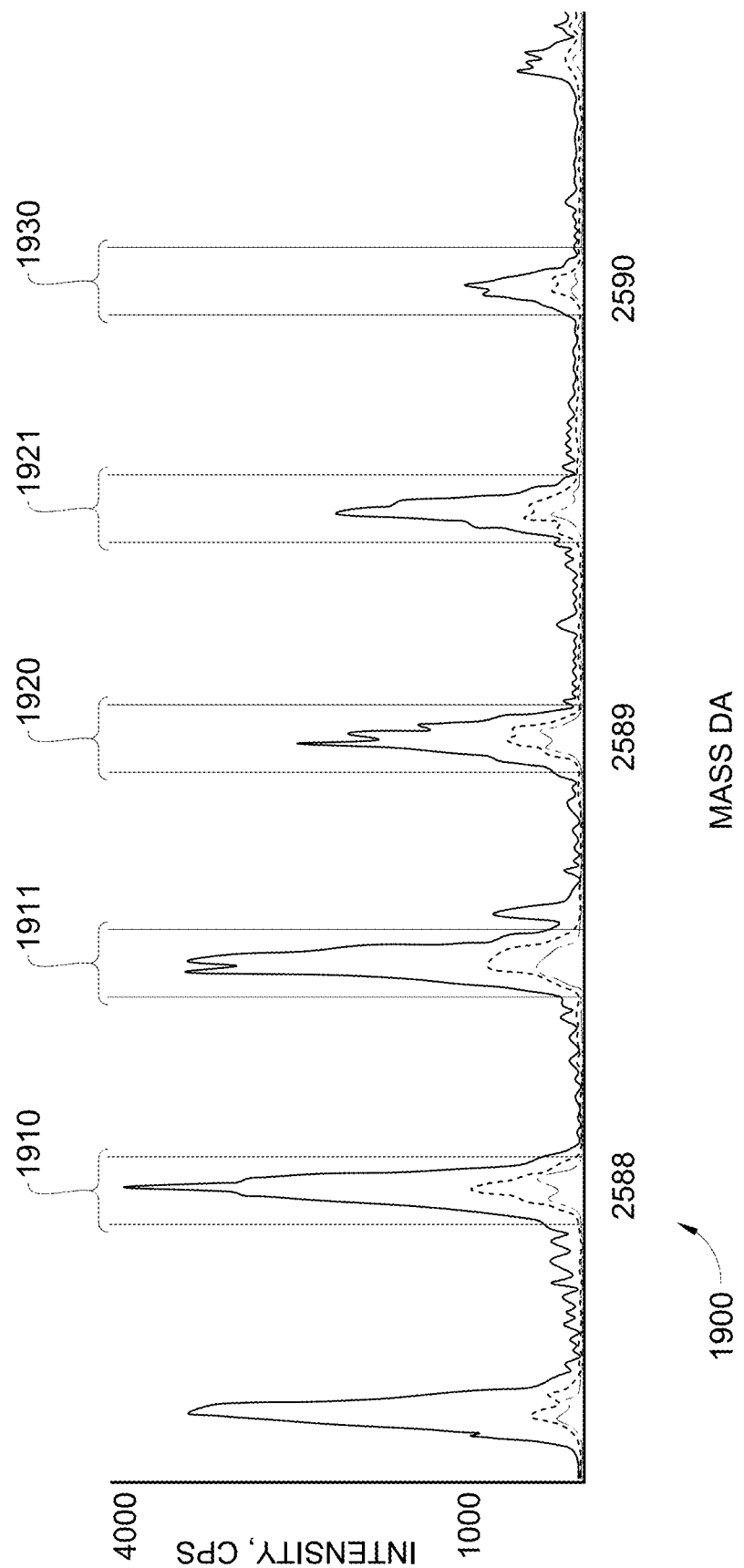
FIG. 19 is an exemplary plot showing peaks that are not real isotopic mass peaks in a zoomed section between 2587 and 2591 Da of 10 overlaid intensity versus MW spectra converted using 10 sequential charge states from an m/z spectrum of a large molecule, in accordance with various embodiments.

FIG. 19 is an exemplary plot 1900 showing peaks that are not real isotopic mass peaks in a zoomed section between 2587 and 2591 Da of 10 overlaid intensity versus MW spectra converted using 10 sequential charge states from an m/z spectrum of a large molecule, in accordance with various embodiments. Initially, it is not known whether or not the section between 2587 and 2591 Da includes real isotopic mass peaks.

Again, in a first step, the 10 overlaid intensity versus MW spectra are searched for aligned molecular peaks that have an intensity above a certain threshold in two or more sequential charge states. Peaks 1910 in the range 2587.91 to 2588.06 Da are found to have an intensity above a certain threshold in two or more sequential charge states, for example.

In a second step, the mass range on either side of peaks 1910 is then searched for aligned isotopic peaks spaced a multiple of 1 Da from peaks 1910. Peaks 1920 and 1930 are found. Peaks 1920 are found in the range 2588.91 to 2589.07 Da. Peaks 1930 are found in the range 2589.94 to 2590.09 Da.

Group of peaks 1910 includes the highest intensity peak. In various embodiments, the peak group with the highest intensity peak is selected. Isotopic peaks are found by moving in steps of 1 Da in increasing mass or 1 Da decreasing mass from the peak group with the highest intensity peak.

In a third step, the percent intensity of each group of isotopic peaks found in the second step is expressed as a function of charge state. The functions of the different groups of isotopic peaks are analyzed and compared. Although performed automatically, this comparison can again be shown graphically.

Figure 20:
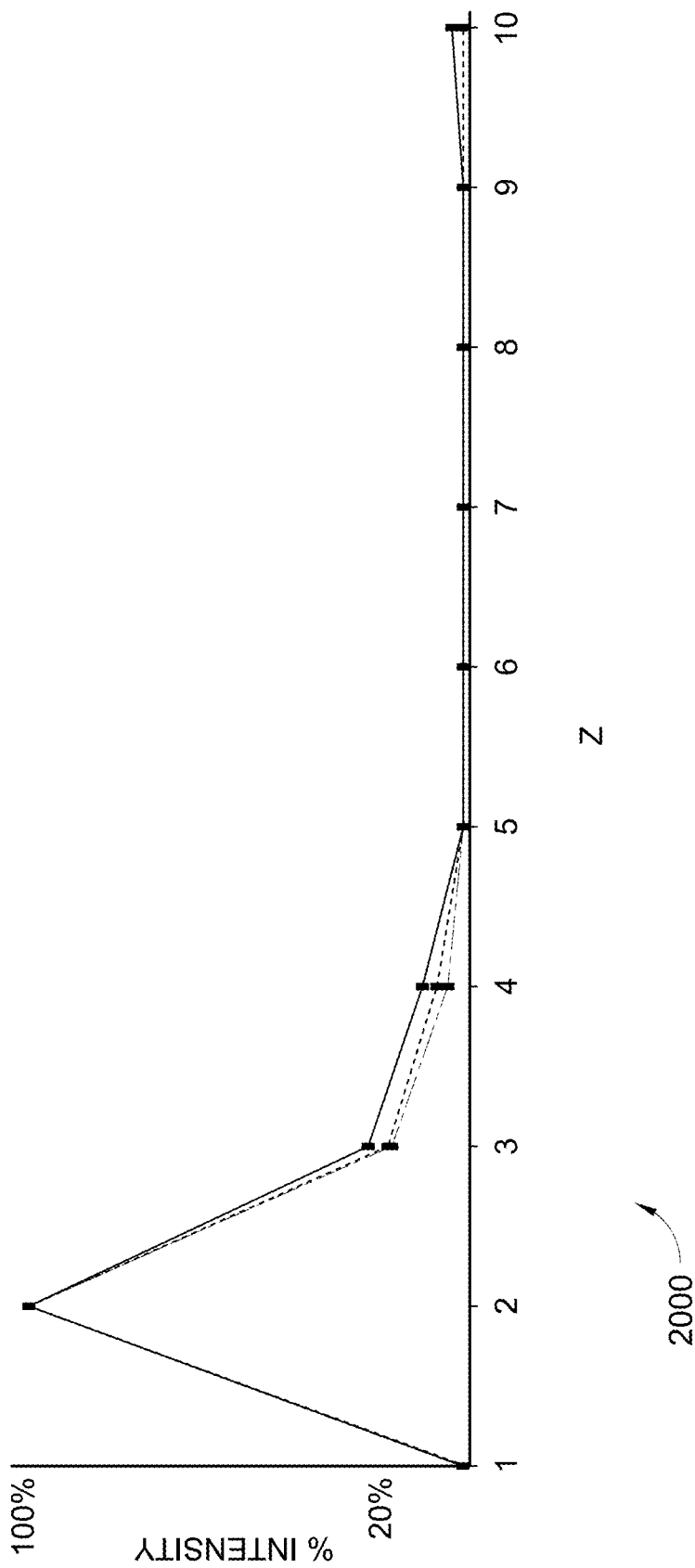
FIG. 20 is an exemplary plot of intensity versus charge state for the three possible isotopic peak groups found from the data of FIG. 19, in accordance with various embodiments.

FIG. 20 is an exemplary plot 2000 of intensity versus charge state for the three possible isotopic peak groups found from the data of FIG. 19, in accordance with various embodiments. In FIG. 20, lines 2010, 2020, and 2030 show how the percent intensities of peaks 1910, 1920, and 1930 of FIG. 19, respectively, vary with charge state.

Lines 2010, 2020, and 2030 of FIG. 20 are analyzed for smooth transitions between charge states and for similar shapes. These lines all have a similar shape. They also all include smooth transitions between charge states.

Figure 21:
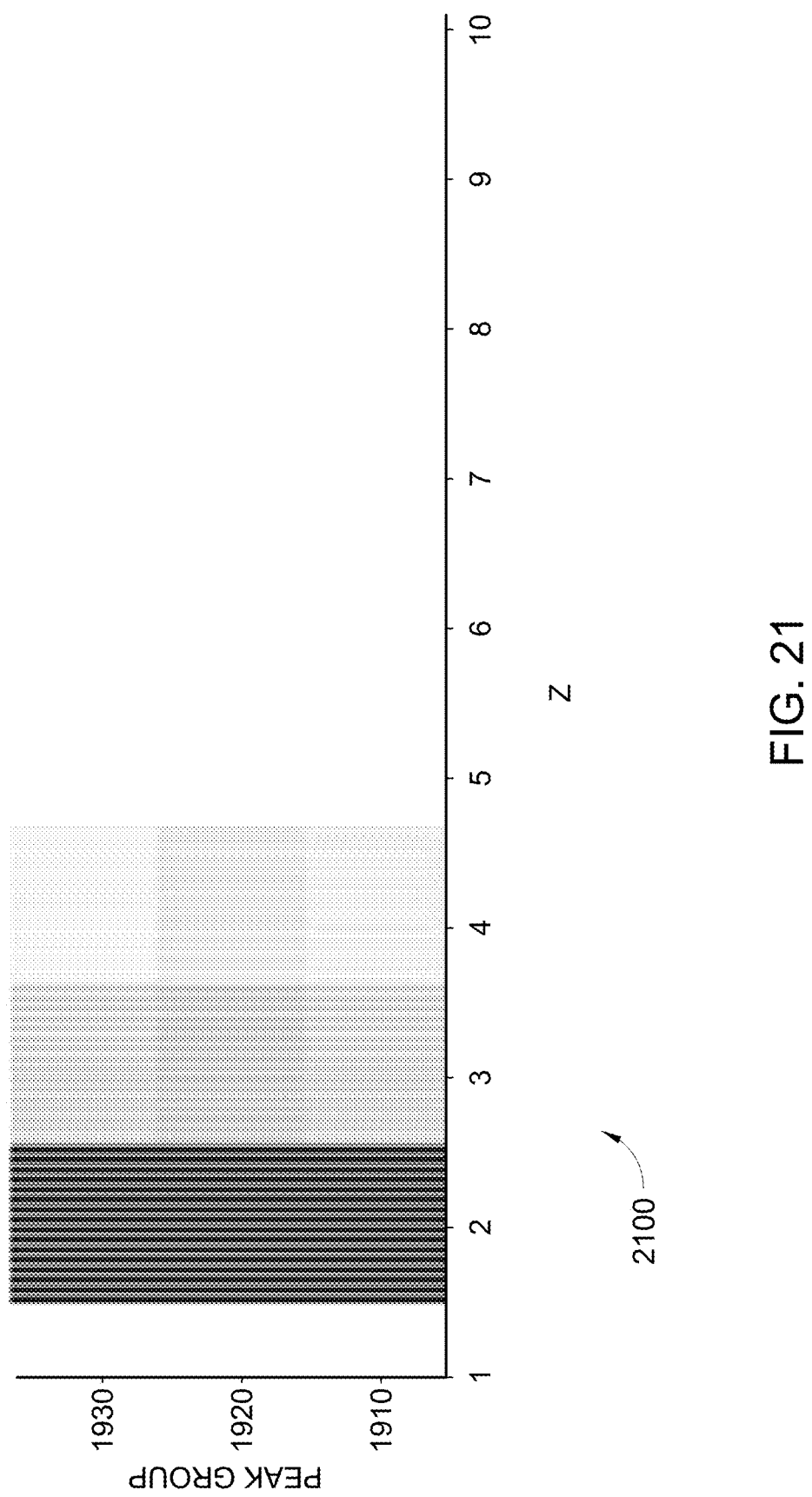
FIG. 21 is an exemplary plot of a 3D heat map of intensity versus charge state for the three possible isotopic peak groups found from the data of FIG. 19, in accordance with various embodiments.

FIG. 21 is an exemplary plot 2100 of a 3D heat map of intensity versus charge state for the three possible isotopic peak groups found from the data of FIG. 19, in accordance with various embodiments. In FIG. 21, the three rows correspond to the three possible isotopic peak groups 1910, 1920, and 1930 (from bottom to top) of FIG. 19. The ten columns of FIG. 21 correspond to the ten charge states. The increasing darkness of each square represents increasing intensity.

Like FIG. 20, FIG. 21 shows that peak groups 1910, 1920, and 1930 all include smooth transitions between charge states. In other words, FIGS. 20 and 21 do not show that the isotopic pattern of FIG. 19 is incorrect.

Returning to FIG. 19, the clue that something is wrong with this isotope pattern is the additional peaks 1911 1921 in the one Da gap between peak groups 1910, 1920, and 1930. As a result, the isotopic pattern of FIG. 19 is incorrect.

FIGS. 13 through 21 graphically depict how an isotope pattern is found and confirmed or not confirmed. However, these figures do not describe how the neutral monoisotopic mass is found.

In various embodiments, the neutral monoisotopic mass is also found along with the correct isotopic pattern. Again, a first step in determining a neutral monoisotopic mass of at least one molecule is to multiply the m/z values of a spectrum that includes the molecule by a range of theoretical charge states.

In a second step, the resulting MW spectra corresponding to the different charge states are aligned by MW and analyzed. The aligned MW spectra (or a matrix of data, which could be either peak intensity or peak area per charge state) are analyzed for peaks above a certain threshold and within a mass tolerance (for example~0.2 Da) in sequential charge states.

Figure 22:
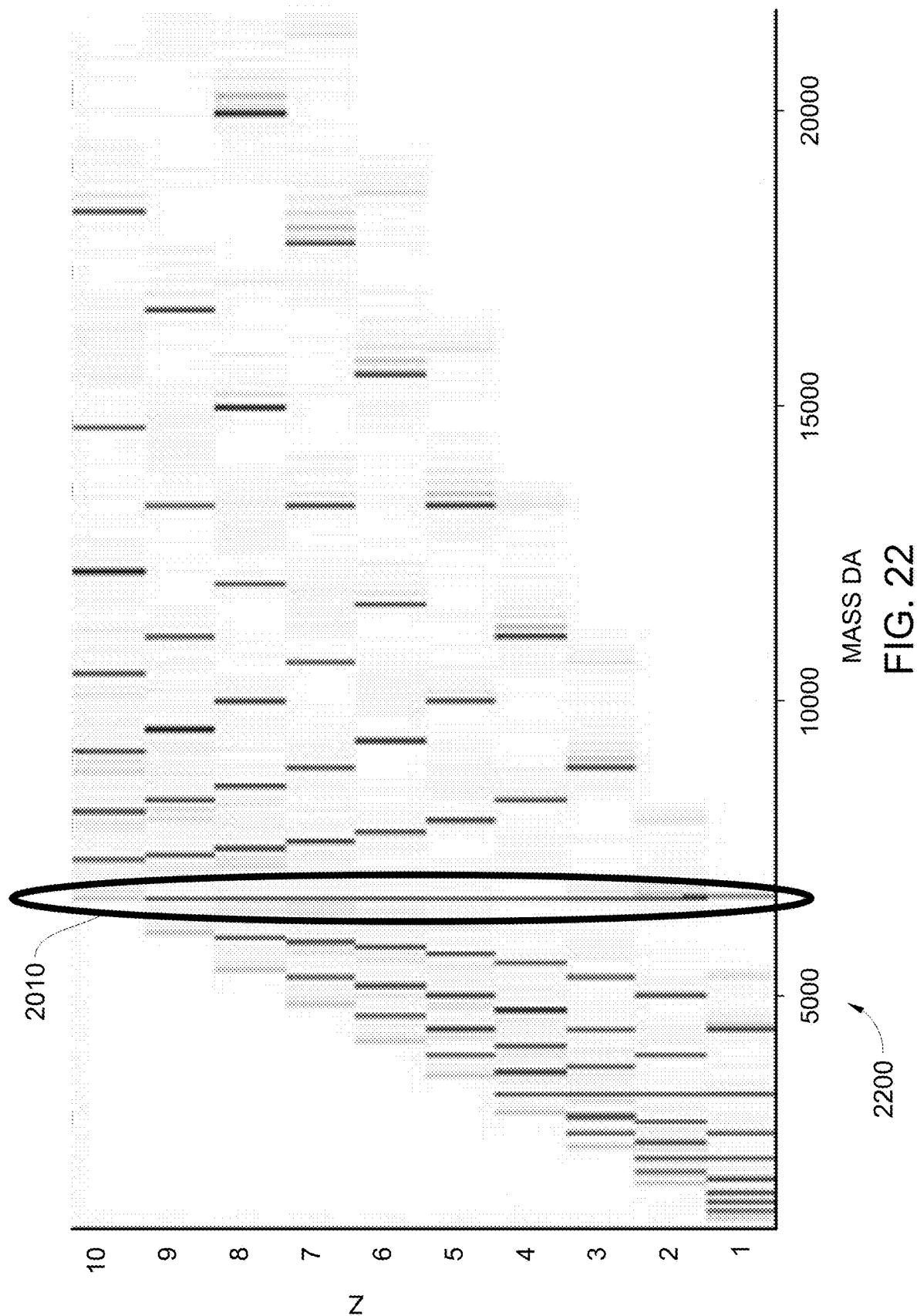
FIG. 22 is an exemplary plot of a 3D heat map showing 10 copies of a single spectrum of a large molecule that have each been converted to an MW spectrum by a different charge state of 10 sequential charge states and aligned by MW, in accordance with various embodiments.

FIG. 22 is an exemplary plot 2200 of a 3D heat map showing 10 copies of a single spectrum of a large molecule that have each been converted to an MW spectrum by a different charge state of 10 sequential charge states and aligned by MW, in accordance with various embodiments. The aligned MW spectra of FIG. 22 are analyzed for peaks above a certain threshold and within a mass tolerance in sequential charge states. Near mass 6656 Da, all 10 sequential charge states include intensity above a certain threshold. These aligned intensities in sequential charge states are obvious in the 3D heat map of FIG. 22 and are highlighted in ellipse 2210. What is not apparent, however, in FIG. 22 is the isotopic pattern near mass 6656 Da.

In a third step, mass pattern filtering is applied to the ten MW mass spectra. The peaks in the mass pattern are 1.0 Da apart. In a fourth step, a consensus isotope pattern is determined. A consensus isotope pattern is, for example, a solution where the relative intensity of isotopes across charge states is maintained within an acceptable error (for example, 15%). The consensus isotope pattern is found, for example, by calculating a relative isotope response, calculating its mean, coefficient of variation (CV), and if the mean is greater than 15%, removing outliers (from both x (charge state) and y (isotope index or mass) dimensions) and recalculating. Also, to find the neutral monoisotopic mass, MO, rules for ratios of the isotope peaks in the cluster are applied (such as in JASMS 2008, 5 (19) 703-712). For example, the ratio of peak I0 and peak I1 should be within some limits (peak I1 cannot be 50 times greater than peak I0—the limits need to be established).

In a fifth step, the consensus isotope pattern is fit to the data. An isotope pattern purity (how much of the isotope pattern fits the consensus one) is then calculated.

In a sixth and final step, for a candidate isotope cluster, just charge states with isotope pattern purity above a certain threshold (e.g., ~ 0.7) are considered. The result with the most subsequent charge states pointing to the same neutral monoisotopic mass, MO, is accepted.

Figure 23:
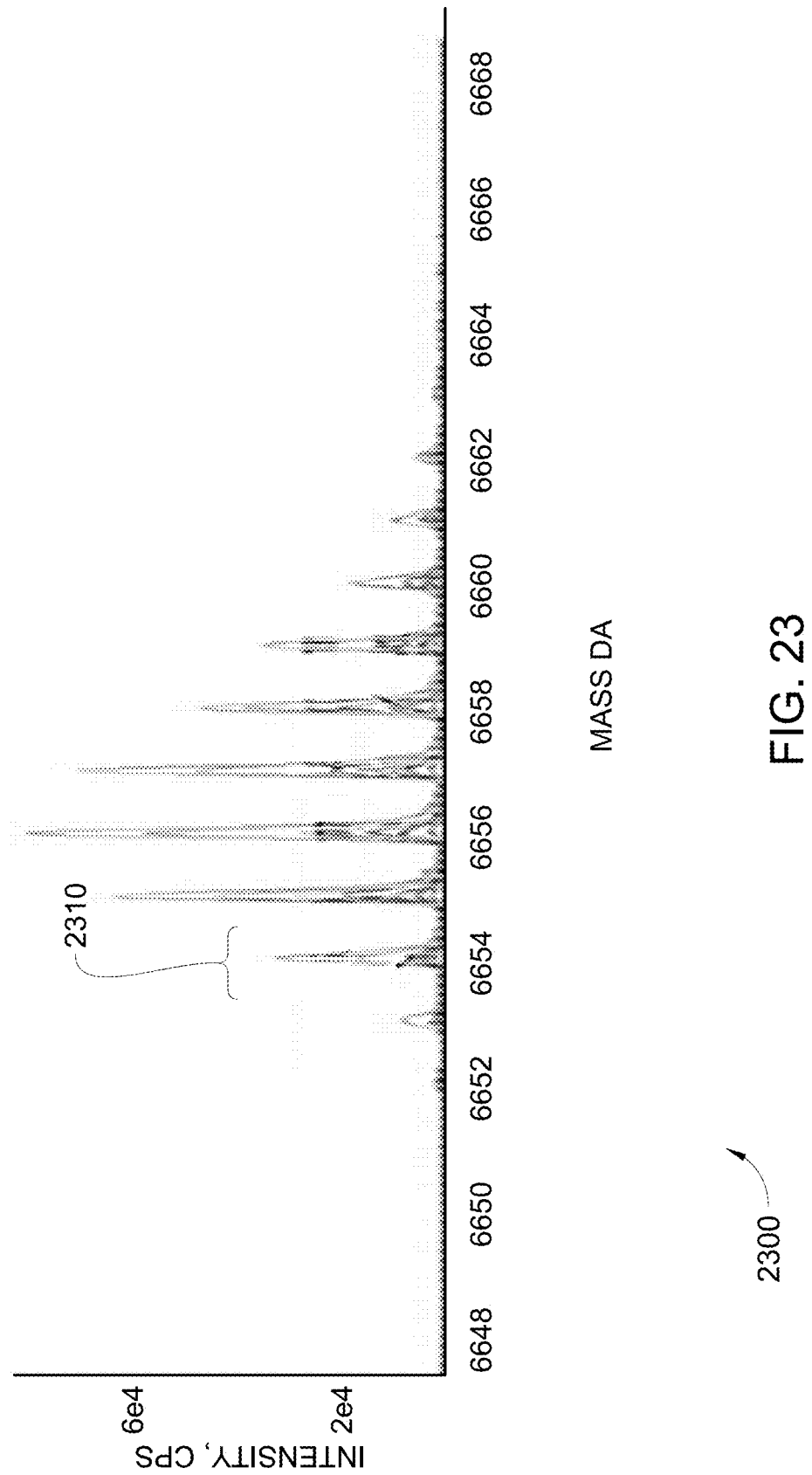
FIG. 23 is an exemplary plot of the 10 MW spectra of FIG. 22 overlaid for the region between 6646 and 6670 Da, in accordance with various embodiments.

FIG. 23 is an exemplary plot 2300 of the 10 MW spectra of FIG. 22 overlaid for the region between 6646 and 6670 Da, in accordance with various embodiments. After applying steps 3-4, as described above, to the data of FIG. 23, a neutral monoisotopic mass, MO, of 6654 is found in nine sequential charge states with isotope pattern purity above 0.7. In other words, peak group 2310 of FIG. 23 is found to include the neutral monoisotopic mass peak.

System for Identifying Neutral Mass Values

Figure 24:
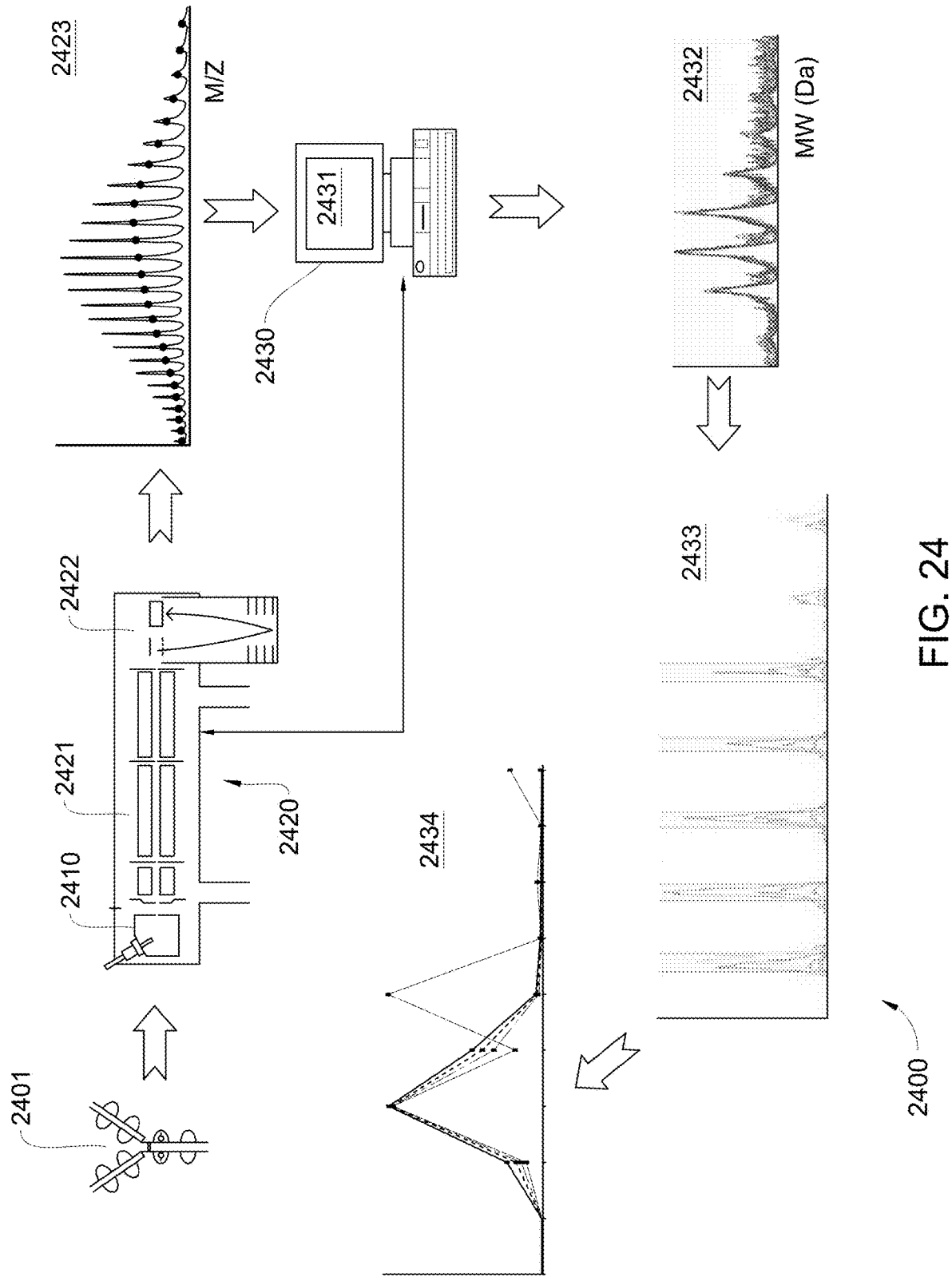
FIG. 24 is a schematic diagram of a system for identifying neutral mass values of at least one molecule in MS, in accordance with various embodiments.

FIG. 24 is a schematic diagram 2400 of a system for identifying neutral mass values of at least one molecule in MS, in accordance with various embodiments. The system of FIG. 24 includes ion source device 2410, mass spectrometer 2420, and processor 2430.

Ion source device 2410 ionizes at least one molecule 2401 of a sample, producing an ion beam. Ion source device 2410 is, for example, an ESI ion source device, but can be any type of ion source device that produces multiple charge states. Ion source device 2410 is shown in FIG. 24 as part of mass spectrometer 2420. However, in various embodiments, ion source device 2410 can be a separate device.

Mass spectrometer 2420 selects an m/z range of ions of the ion beam using a mass filter 2421. Mass spectrometer 2420 mass analyzes the m/z range using a mass analyzer 2422, producing mass spectrum 2423. Mass spectrometer 2420 performs an MS scan, for example. Mass spectrometer 2420 is shown in FIG. 24 as a quadrupole time-of-flight (Q-TOF) device. However, mass spectrometer 1120 can be any type of mass spectrometer. Mass filter 2421 is shown as a quadrupole, for example. However, mass filter 532 can be any type of mass filter. Mass analyzer 2422 is shown as a TOF mass analyzer, for example. However, mass analyzer 2422 can be any type of mass analyzer. Mass analyzer 2422 can include, but is not limited to, a quadrupole, an ion trap, a linear ion trap, an orbitrap, a magnetic four-sector mass analyzer, a hybrid quadrupole time-of-flight (Q-TOF) mass analyzer, or a Fourier transform mass analyzer.

Processor 2430 is in communication with ion source device 2410 and mass spectrometer 2420. Processor 2430 can be, but is not limited to, the system of FIG. 1, a computer, microprocessor, microcontroller, or any device capable of sending and receiving control signals and data to and from ion source device 2410 and mass spectrometer 2420 and other devices. Processor 2430 further has access to one or more memory devices, like the system of FIG. 1.

Processor 2430 receives a range of N sequential charge states. Processor 2430 receives the range from a user or retrieves a previously stored range from a memory device, for example. Processor 2430 creates a copy of the mass spectrum for each of the N charge states, producing N m/z spectra. Processor 2430 converts each spectrum of the N spectra to a neutral mass mass spectrum using a different charge state of the N charge states, producing N neutral mass mass spectra. Processor 2430 aligns the N neutral mass mass spectra by neutral mass. Finally, when two or more spectra of the N neutral mass mass spectra corresponding to two or more different and sequential charge states include a neutral mass peak above a predetermined intensity threshold at a neutral mass value within a predetermined neutral mass tolerance, processor 2430 identifies the neutral mass value as a neutral mass of at least one molecule 2401.

In various embodiments, the system of FIG. 24 further includes a display device, such as display 2431. Processor 2430 further displays on the display device a three-dimensional (3D) heat map of the aligned N neutral mass mass spectra. For example, each spectrum of the N neutral mass mass spectra is a row of the 3D heat map and each row corresponds to a sequential charge state of the N charge states. An exemplary 3D is shown in FIG. 6, for example.

In various embodiments, colors or shading in each row of the 3D heat map represent peak intensity. In various alternative embodiments, colors or shading in each row of the 3D heat map represent peak area per charge state.

Returning to FIG. 24, in various embodiments, processor 2430 further displays on the display device each of the aligned N neutral mass mass spectra overlaid on top of each other, such as in plot 2432.

In various embodiments, processor 2430 further normalizes intensities of each of the aligned N neutral mass mass spectra before identifying the neutral mass value. For example, processor 2430 normalizes intensities of each spectrum of the aligned N neutral mass mass spectra by dividing an intensity of each peak of the spectrum by an intensity of the highest intensity peak of the spectrum.

In various embodiments, processor 2430 identifies a plurality of neutral mass values for the at least one molecule.

In various embodiments, processor 2430 identifies two or more neutral mass values of the plurality of neutral mass values as an isotopic cluster if adjacent neutral mass values of the two or more neutral mass values are separated from one another by about 1 Da (or on the order of 1 Da) within a predetermined isotopic neutral mass tolerance. For example, four neutral mass values are identified as an isotopic cluster in plot 2433.

In various embodiments, processor 2430 further confirms the isotopic cluster by performing a number of steps. First, processor 2430 calculates an intensity versus charge function for each neutral mass value of the two or more neutral mass values that describes how the intensity at each neutral mass value varies with the N sequential charge states. One or more intensity versus charge functions are produced, such as the four intensity versus charge functions shown in plot 2434. Second, processor 2430 compares shapes of the one or more intensity versus charge functions within a predetermined shape comparison tolerance. For example, maximum intensities and areas of the functions can be compared. Finally, processor 2430 confirms the isotopic cluster if the neutral mass values of the two or more neutral mass values have the same intensity versus charge function shapes within the predetermined shape comparison tolerance.

In various embodiments, processor 2430 further confirms the isotopic cluster using an additional step. Processor 2430 analyzes each function of the one or more intensity versus charge functions for local maxima. Processor 2430 confirms the isotopic cluster if one local maximum is found for each function and the local maxima are within a given tolerance (in charge) from one another.

In various embodiments, processor 2430 further calculates a neutral monoisotopic mass value for the isotopic cluster.

In various embodiments, processor 2430 further confirms the isotopic cluster by analyzing the N neutral mass mass spectra for peaks between the two or more neutral mass values that have intensities above the predetermined intensity. Processor 2430 confirms the isotopic cluster if a majority of peaks found between the two or more neutral mass values do not have intensities above the predetermined intensity. As described above, FIG. 19 shows a case in which peaks are found between the two or more neutral mass values that have intensities above the predetermined intensity.

In various embodiments, processor 2430 further confirms the isotopic cluster by finding other isotopic clusters that exist in different adjacent charge states, such as clusters 610, 620, 630, and 650 in FIG. 6. Returning to FIG. 24, specifically processor 2430 further confirms the isotopic cluster by identifying a second group of two or more neutral mass values of the plurality of neutral mass values for the at least one molecule as a second isotopic cluster if adjacent neutral mass values of the two or more neutral mass values are separated from one another by an isotope spacing on the order of 1 Da within a predetermined isotopic neutral mass tolerance.

Method for Identifying Neutral Mass Values

Figure 25:
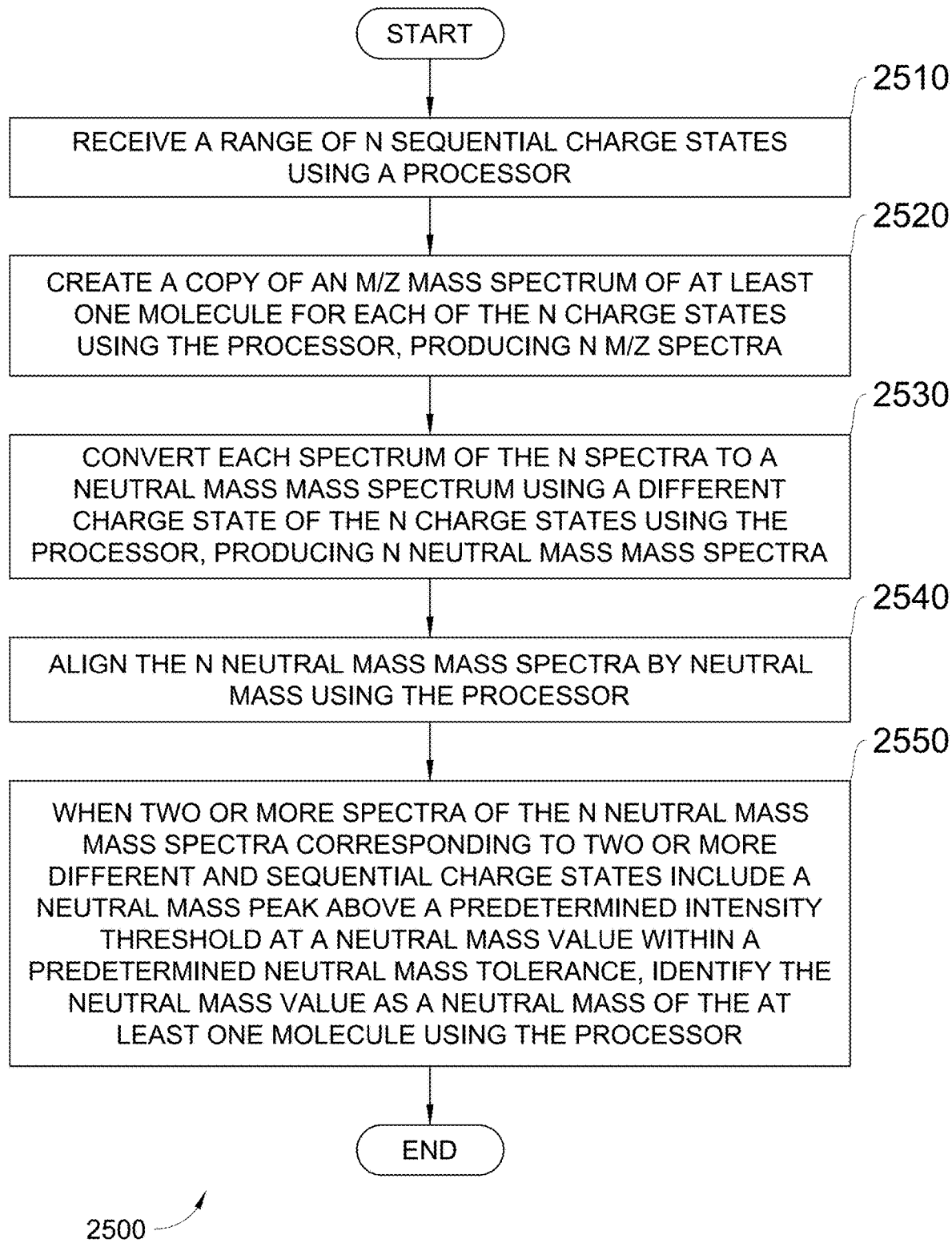
FIG. 25 is a flowchart showing a method for identifying neutral mass values of at least one molecule in MS, in accordance with various embodiments.

FIG. 25 is a flowchart showing a method 2500 for identifying neutral mass values of at least one molecule in MS, in accordance with various embodiments.

In step 2510 of method 2500, a range of N sequential charge states is received using a processor.

In step 2520, a copy of an m/z mass spectrum of at least one molecule is created for each of the N charge states using the processor, producing N m/z spectra. The mass spectrum is produced by a mass spectrometer that selects an m/z range of ions of an ion beam and mass analyzes the m/z range. The ion beam is produced by an ion source device that ionizes the at least one molecule of a sample.

In step 2530, each spectrum of the N spectra is converted to a neutral mass mass spectrum using a different charge state of the N charge states using the processor, producing N neutral mass mass spectra.

In step 2540, the N neutral mass mass spectra are aligned by neutral mass using the processor.

In step 2550, when two or more spectra of the N neutral mass mass spectra corresponding to two or more different and sequential charge states include a neutral mass peak above a predetermined intensity threshold at a neutral mass value within a predetermined neutral mass tolerance, the neutral mass value is identified as a neutral mass of the at least one molecule using the processor.

Computer Program Product for Identifying Neutral Mass Values

In various embodiments, computer program products include a tangible computer-readable storage medium whose contents include a program with instructions being executed on a processor so as to perform a method for identifying neutral mass values of at least one molecule in MS. This method is performed by a system that includes one or more distinct software modules.

Figure 26:
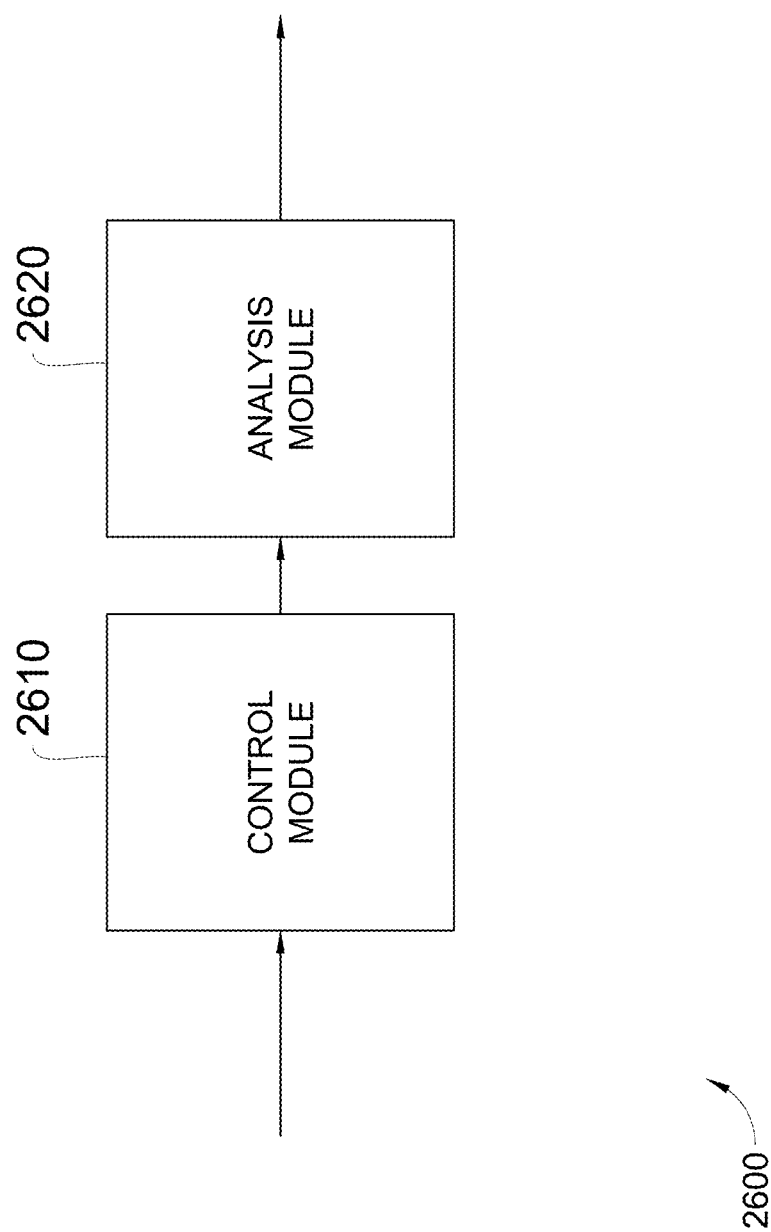
FIG. 26 is a schematic diagram of a system that includes one or more distinct software modules that perform a method for identifying neutral mass values of at least one molecule in MS, in accordance with various embodiments.

FIG. 26 is a schematic diagram of a system 2600 that includes one or more distinct software modules that perform a method for identifying neutral mass values of at least one molecule in MS, in accordance with various embodiments. System 2600 includes a control module 2610 and an analysis module 2620.

Control module 2610 instructs an ion source device to ionize at least one molecule of a sample, producing an ion beam. Control module 2610 instructs a mass spectrometer to select an m/z range of ions of the ion beam. Control module 2610 instructs the mass spectrometer to mass analyze the m/z range, producing a mass spectrum.

Analysis module 2620 receives a range of N sequential charge states. Analysis module 2620 creates a copy of the mass spectrum for each of the N charge states, producing N m/z spectra. Analysis module 2620 converts each spectrum of the N spectra to a neutral mass mass spectrum using a different charge state of the N charge states, producing N neutral mass mass spectra. Analysis module 2620 aligns the N neutral mass mass spectra by neutral mass. When two or more spectra of the N neutral mass mass spectra corresponding to two or more different and sequential charge states include a neutral mass peak above a predetermined intensity threshold at a neutral mass value within a predetermined neutral mass tolerance, analysis module 2620 identifies the neutral mass value as a neutral mass of the at least one molecule.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for identifying neutral mass values of at least one molecule in mass spectrometry (MS), comprising:
    an ion source device that ionizes at least one molecule of a sample, producing an ion beam;
    a mass spectrometer that selects a mass-to-charge ratio (m/z) range of ions of the ion beam and mass analyzes the m/z range, producing a mass spectrum; and
    a processor that
        receives a range of N sequential charge states,
        creates a copy of the mass spectrum for each of the N charge states, producing N m/z spectra,
        converts each spectrum of the N spectra to a neutral mass mass spectrum using a different charge state of the N charge states, producing N neutral mass mass spectra,
        aligns the N neutral mass mass spectra by neutral mass, and
        when two or more spectra of the N neutral mass mass spectra corresponding to two or more different and sequential charge states include a neutral mass peak above a predetermined intensity threshold at a neutral mass value within a predetermined neutral mass tolerance, identifying the neutral mass value as a neutral mass of the molecule.

2. The system of claim 1, further comprising a display device, wherein the processor further displays on the display device a three-dimensional (3D) heat map of the aligned N neutral mass mass spectra, wherein each spectrum of the N neutral mass mass spectra is a row of the 3D heat map and each row corresponds to a sequential charge state of the N charge states.

3. The system of claim 2, wherein colors or shading in each row of the 3D heat map represent peak intensity.

4. The system of claim 2, wherein colors or shading in each row of the 3D heat map represent peak area per charge state.

5. The system of claim 1, further comprising a display device, wherein the processor further displays on the display device each of the aligned N neutral mass mass spectra overlaid on top of each other.

6. The system of claim 1, wherein the processor further normalizes intensities of each of the aligned N neutral mass mass spectra before identifying the neutral mass value.

7. The system of claim 6, wherein the processor normalizes intensities of each spectrum of the aligned N neutral mass mass spectra by dividing an intensity of each peak of the spectrum by an intensity of a highest intensity peak of the spectrum.

8. The system of claim 1, wherein the processor identifies two or more neutral mass values of a plurality of neutral mass values for the at least one molecule as an isotopic cluster if adjacent neutral mass values of the two or more neutral mass values are separated from one another by an isotope spacing on the order of 1 Da within a predetermined isotopic neutral mass tolerance.

9. The system of claim 8, wherein the processor further confirms the isotopic cluster by
    calculating an intensity versus charge function for each neutral mass value of the two or more neutral mass values that describes how the intensity at each neutral mass value varies with the N sequential charge states, producing one or more intensity versus charge functions,
    comparing shapes of the one or more intensity versus charge functions within a predetermined shape comparison tolerance, and
    confirming the isotopic cluster if the neutral mass values of the two or more neutral mass values have similar intensity versus charge function shapes within the predetermined shape comparison tolerance.

10. The system of claim 9, wherein the processor further confirms the isotopic cluster by analyzing each function of the one or more intensity versus charge functions for local maxima, and
    confirming the isotopic cluster if one local maximum is found for each function and the local maxima are within a given tolerance (in charge) from one another.

11. The system of claim 8, wherein the processor further determines a neutral monoisotopic mass value for the isotopic cluster.

12. The system of claim 8, wherein the processor further confirms the isotopic cluster by
    analyzing the N neutral mass mass spectra for peaks between the two or more neutral mass values that have intensities above the predetermined intensity, and
    if a majority of peaks found between the two or more neutral mass values do not have intensities above the predetermined intensity, the isotopic cluster is confirmed.

13. The system of claim 8, wherein the processor further confirms the isotopic cluster by identifying a second group of two or more neutral mass values of the plurality of neutral mass values for the at least one molecule as a second isotopic cluster if adjacent neutral mass values of the two or more neutral mass values are separated from one another by an isotope spacing on the order of 1 Da within a predetermined isotopic neutral mass tolerance.

14. A method for identifying neutral mass values of at least one molecule in mass spectrometry (MS), comprising:
receiving a range of N sequential charge states using the processor;
creating a copy of a mass-to-charge ratio (m/z) mass spectrum for each of the N charge states using the processor, producing N m/z spectra, wherein the mass spectrum is produced by a mass spectrometer that selects an m/z range of ions of an ion beam and mass analyzes the m/z range and wherein the ion beam is produced by an ion source device that ionizes at least one molecule of a sample;
converting each spectrum of the N spectra to a neutral mass mass spectrum using a different charge state of the N charge states using the processor, producing N neutral mass mass spectra;
aligning the N neutral mass mass spectra by neutral mass using the processor; and
when two or more spectra of the N neutral mass mass spectra corresponding to two or more different and sequential charge states include a neutral mass peak above a predetermined intensity threshold at a neutral mass value within a predetermined neutral mass tolerance, identifying the neutral mass value as a neutral mass of the at least one molecule using the processor.

15. A computer program product, comprising a non-transitory and tangible computer-readable storage medium whose contents include a program with instructions being executed on a processor to perform a method for identifying neutral mass values of at least one molecule in mass spectrometry (MS), the method comprising:
providing a system, wherein the system comprises one or more distinct software modules, and wherein the distinct software modules comprise a control module and an analysis module;
instructing an ion source device to ionize at least one molecule of a sample using the control module, producing an ion beam;
instructing a mass spectrometer that selects a mass-to-charge ratio (m/z) range of ions of the ion beam and mass analyzes the m/z range using the control module, producing a mass spectrum; and
receiving a range of N sequential charge states using the analysis module;
creating a copy of the mass spectrum for each of the N charge states using the analysis module, producing N m/z spectra;
converting each spectrum of the N spectra to a neutral mass mass spectrum using a different charge state of the N charge states using the analysis module, producing N neutral mass mass spectra;
aligning the N neutral mass mass spectra by neutral mass using the analysis module; and
when two or more spectra of the N neutral mass mass spectra corresponding to two or more different and sequential charge states include a neutral mass peak above a predetermined intensity threshold at a neutral mass value within a predetermined neutral mass tolerance, identifying the neutral mass value as a neutral mass of the at least one molecule using the analysis module.

* * * * *